United States Patent
Batchu et al.

(10) Patent No.: US 11,090,334 B2
(45) Date of Patent: Aug. 17, 2021

(54) CHIMERIC ANTIGEN RECEPTOR SPECIFIC TO B-CELL MATURATION ANTIGEN, A RECOMBINANT EXPRESSION VECTOR AND A METHOD THEREOF

(71) Applicant: MED MANOR ORGANICS, (P) LTD, Hyderabad (IN)

(72) Inventors: Ramesh B. Batchu, Royal Oak, MI (US); Donald W. Weaver, Dearborn Heights, MI (US); Jose Edson Silva Pontes, Old Mission, MI (US)

(73) Assignee: MED MANOR ORGANICS (P) LTD.

( * ) Notice: Subject to any disclaimer, the term of this patent is extended or adjusted under 35 U.S.C. 154(b) by 0 days.

(21) Appl. No.: 16/073,575

(22) PCT Filed: Jan. 28, 2017

(86) PCT No.: PCT/IN2017/050040
§ 371 (c)(1),
(2) Date: Jul. 27, 2018

(87) PCT Pub. No.: WO2017/130223
PCT Pub. Date: Aug. 3, 2017

(65) Prior Publication Data
US 2020/0405758 A1 Dec. 31, 2020

(30) Foreign Application Priority Data
Jan. 29, 2016 (IN) .............................. 201641003422

(51) Int. Cl.
*A61K 35/17* (2015.01)
*A61K 35/13* (2015.01)
*C07K 16/30* (2006.01)
*C07K 14/705* (2006.01)
*C07K 14/725* (2006.01)
*C07K 16/28* (2006.01)
*A61K 45/06* (2006.01)

(52) U.S. Cl.
CPC .......... *A61K 35/17* (2013.01); *C07K 14/7051* (2013.01); *C07K 14/70521* (2013.01); *C07K 16/2878* (2013.01); *A61K 45/06* (2013.01); *C07K 2317/565* (2013.01); *C07K 2317/622* (2013.01); *C07K 2319/03* (2013.01); *C07K 2319/33* (2013.01)

(58) Field of Classification Search
None
See application file for complete search history.

(56) References Cited

FOREIGN PATENT DOCUMENTS

| | | |
|---|---|---|
| WO | 2013154760 A1 | 10/2013 |
| WO | 2014138704 A1 | 9/2014 |
| WO | 2014179759 A1 | 11/2014 |
| WO | 2015158671 A1 | 10/2015 |
| WO | 2015188119 A1 | 12/2015 |
| WO | 2016014565 A2 | 1/2016 |
| WO | 2016014789 A2 | 1/2016 |
| WO | 2015052538 A1 | 4/2016 |
| WO | 2016090369 A1 | 6/2016 |

OTHER PUBLICATIONS

Van der Schans et al, Dual Targeting to Overcome Current Challenges in Multiple Myeloma CAR T-Cell Treatment, Frontiers in Oncology, 2020, pp. 1-8.*
García-Guerrero et al, Overcoming Chimeric Antigen Receptor (CAR) Modified T-Cell Therapy Limitations in Multiple Myeloma, Frontiers in Immunology 2020, pp. 1-17.*
Sneha Ramakrishna et al, Prospects and challenges for use of CAR T cell therapies in solid tumors, Expert Opinion on Biological Therapy, 2020, 20:5, 503-516.*
Mirzaei et al, Chimeric Antingen Receptors T cell Therapy in SOlid Tumors: Challeges and Clinical Applications, 2017, Frontiers in Immunology, pp. 1-13.*
Ramos, C.A., et al., "CAR-T Cell Therapy for Lymphoma", Annual Review of Medicine: Selected Topics in the Clinicalsciences, vol. 67, No. 1, pp. 165-183 (2016).

* cited by examiner

*Primary Examiner* — Maria Marvich
(74) *Attorney, Agent, or Firm* — Holland & Hart LLP

(57) ABSTRACT

A chimeric antigen receptors (CARs) specific to B-cell maturation antigen (BCMA), a recombinant expression vector and a method for the development of the genetically modified immune effector cells especially natural killer-92 cells (NK-92 cells) that target Multiple Myeloma (MM) and other hematological malignancies. The invention encompasses a single chain variable region (scFv) from BCMA specific antibody fused via transmembrane domain to intracellular signaling domain and two co-stimulatory molecules. Expression of CARs across the plasma membrane of immune effector cells such as natural killer cells (NK cells), NK-92 cells, T lymphocytes (T cells) and natural killer T cells (NKT cells) with exposed scFv interacting with the BCMA tumor target. The interaction initiates cascade of events through the intracellular stimulatory and signaling domains leading to the activation of immune effector cells followed by lysis of the tumor. The invention also includes methods of administering a genetically modified immune effector cells expressing a CAR that comprises a BCMA binding domain. FIG. 4 is the representative figure.

9 Claims, 12 Drawing Sheets
Specification includes a Sequence Listing.

SEQUENCE LISTING

<160> NUMBER OF SEQ ID NOS: 59

<210> SEQ ID NO 1
<211> LENGTH: 13
<212> TYPE: PRT
<213> ORGANISM: Homo sapiens

<400> SEQUENCE: 1

Ala Ala Leu Ser Ala Thr Glu Ile Glu Lys Ser Ile Ser
1               5                   10

<210> SEQ ID NO 2
<211> LENGTH: 15
<212> TYPE: PRT
<213> ORGANISM: Homo sapiens

<400> SEQUENCE: 2

Cys Pro Ala Ala Leu Ser Ala Thr Glu Ile Glu Lys Ser Ile Ser
1               5                   10                  15

<210> SEQ ID NO 3
<211> LENGTH: 417
<212> TYPE: DNA
<213> ORGANISM: Homo sapiens

<400> SEQUENCE: 3

```
atggcttggg tgtggacctt gctattcctg atggcagctg cccaaagtgc caagcacag      60 atccagttgg tgcagtctgg acctgagctg aagaagcctg gagagacagt caagatctcc    120
tgcaaggctt ctggatatac cttcacaaac tctggaatga ctgggtgaa gcaggctcca     180 ggaaagggtt taaagtggat gggctggata aacacctaca ctggagagcc aacatatgct    240
gatgacttca agggacggtt tgccttctct ttggaaacct ctgccagcac tgcctatttg    300
cagatcaaca acctcaaaaa tgaggacacg gctacatatt tctgtgtaag agcgggcagc    360
tacaggaact atgctatgga ctactgggt caaggaacct cagtcaccgt ctcctca        417
```

<210> SEQ ID NO 4
<211> LENGTH: 139
<212> TYPE: PRT
<213> ORGANISM: Homo sapiens

<400> SEQUENCE: 4

```
Met Ala Trp Val Trp Thr Leu Leu Phe Leu Met Ala Ala Ala Gln Ser
1               5                   10                  15

Ala Gln Ala Gln Ile Gln Leu Val Gln Ser Gly Pro Glu Leu Lys Lys
            20                  25                  30

Pro Gly Glu Thr Val Lys Ile Ser Cys Lys Ala Ser Gly Tyr Thr Phe
        35                  40                  45

Thr Asn Ser Gly Met Asn Trp Val Lys Gln Ala Pro Gly Lys Gly Leu
    50                  55                  60

Lys Trp Met Gly Trp Ile Asn Thr Tyr Thr Gly Glu Pro Thr Tyr Ala
65              70                  75                  80

Asp Asp Phe Lys Gly Arg Phe Ala Phe Ser Leu Glu Thr Ser Ala Ser
                85                  90                  95

Thr Ala Tyr Leu Gln Ile Asn Asn Leu Lys Asn Glu Asp Thr Ala Thr
            100                 105                 110

Tyr Phe Cys Val Arg Ala Gly Ser Tyr Arg Asn Tyr Ala Met Asp Tyr
        115                 120                 125

Trp Gly Gln Gly Thr Ser Val Thr Val Ser Ser
    130                 135

<210> SEQ ID NO 5
<211> LENGTH: 30
<212> TYPE: DNA
<213> ORGANISM: Homo sapiens

<400> SEQUENCE: 5
ggatatacct tcacaaactc tggaatgaac                                    30

<210> SEQ ID NO 6
<211> LENGTH: 30
<212> TYPE: PRT
<213> ORGANISM: Homo sapiens

<400> SEQUENCE: 6

Gly Leu Tyr Thr Tyr Arg Thr His Arg Pro His Glu Thr His Arg Ala
1               5                   10                  15

Ser Asn Ser Glu Arg Gly Leu Tyr Met Glu Thr Ala Ser Asn
            20                  25                  30

<210> SEQ ID NO 7
<211> LENGTH: 51
<212> TYPE: DNA
<213> ORGANISM: Homo sapiens

<400> SEQUENCE: 7
tggataaaca cctacactgg agagccaaca tatgctgatg acttcaaggg a            51

<210> SEQ ID NO 8
<211> LENGTH: 17
<212> TYPE: PRT
<213> ORGANISM: Homo sapiens

<400> SEQUENCE: 8

Trp Ile Asn Thr Tyr Thr Gly Glu Pro Thr Tyr Ala Asp Asp Phe Lys
1               5                   10                  15

Gly

<210> SEQ ID NO 9
<211> LENGTH: 34
<212> TYPE: DNA
```

<210> SEQ ID NO 9
<211> LENGTH: 34
<212> TYPE: DNA
<213> ORGANISM: Homo sapiens

<400> SEQUENCE: 9
gcgggcagct acaggaacta tgctatggac tact    34

<210> SEQ ID NO 10
<211> LENGTH: 11
<212> TYPE: PRT
<213> ORGANISM: Homo sapiens

<400> SEQUENCE: 10

Ala Gly Ser Tyr Arg Asn Tyr Ala Met Asp Tyr
1               5                   10

<210> SEQ ID NO 11
<211> LENGTH: 396
<212> TYPE: DNA
<213> ORGANISM: Homo sapiens

<400> SEQUENCE: 11
atgaggtgcc tagctgagtt cctggggctg cttgtgctct ggatccctgg agccattggg    60
gatattgtga tgactcaggc tgcaccctct gtacttgtca ctcctggaga gtcagtatcc   120
atctcctgca ggtctagtaa gagtctcctg tatggtaatg caacacttac ttgtattgg   180 ttcctgcaga ggccaggcca gtctcctcag ctcctgatat atcggatgtc aaccttgcc   240 tcaggagtcc cagacaggtt cagtggcagt gggtcaggaa ctgctttcac actgagaatc   300
agtagagtgg aggctgagga tgtgggtgtt tattactgta tgcaacatct agaatatccg   360
ctcacgttcg gtgctgggac caagctggag ctgaaa                             396

<210> SEQ ID NO 12
<211> LENGTH: 132
<212> TYPE: PRT
<213> ORGANISM: Homo sapiens

<400> SEQUENCE: 12

Met Arg Cys Leu Ala Glu Phe Leu Gly Leu Leu Val Leu Trp Ile Pro
1               5                   10                  15

Gly Ala Ile Gly Asp Ile Val Met Thr Gln Ala Ala Pro Ser Val Leu
                20                  25                  30

Val Thr Pro Gly Glu Ser Val Ser Ile Ser Cys Arg Ser Ser Lys Ser
            35                  40                  45

Leu Leu Tyr Gly Asn Gly Asn Thr Tyr Leu Tyr Trp Phe Leu Gln Arg
        50                  55                  60

Pro Gly Gln Ser Pro Gln Leu Leu Ile Tyr Arg Met Ser Asn Leu Ala
65                  70                  75                  80

Ser Gly Val Pro Asp Arg Phe Ser Gly Ser Gly Ser Gly Thr Ala Phe
                85                  90                  95

Thr Leu Arg Ile Ser Arg Val Glu Ala Glu Asp Val Gly Val Tyr Tyr
            100                 105                 110

Cys Met Gln His Leu Glu Tyr Pro Leu Thr Phe Gly Ala Gly Thr Lys
        115                 120                 125

Leu Glu Leu Lys
    130

<210> SEQ ID NO 13
<211> LENGTH: 48
<212> TYPE: DNA
<213> ORGANISM: Homo sapiens

<400> SEQUENCE: 13
aggtctagta agagtctcct gtatggtaat ggcaacactt acttgtat        48

<210> SEQ ID NO 14
<211> LENGTH: 16
<212> TYPE: PRT
<213> ORGANISM: Homo sapiens

<400> SEQUENCE: 14

Arg Ser Ser Lys Ser Leu Leu Tyr Gly Asn Gly Asn Thr Tyr Leu Tyr
1               5                   10                  15

<210> SEQ ID NO 15
<211> LENGTH: 21
<212> TYPE: DNA
<213> ORGANISM: Homo sapiens

<400> SEQUENCE: 15
cggatgtcca accttgcctc a        21

<210> SEQ ID NO 16
<211> LENGTH: 7
<212> TYPE: PRT
<213> ORGANISM: Homo sapiens

<400> SEQUENCE: 16

Pro Gly Gln Ser Pro Gln Leu
1               5

<210> SEQ ID NO 17
<211> LENGTH: 27
<212> TYPE: DNA
<213> ORGANISM: Homo sapiens

<400> SEQUENCE: 17
atgcaacatc tagaatatcc gctcacg        27

<210> SEQ ID NO 18
<211> LENGTH: 9
<212> TYPE: PRT
<213> ORGANISM: Homo sapiens

<400> SEQUENCE: 18

Glu Ala Glu Asp Val Gly Val Tyr Tyr
1               5

<210> SEQ ID NO 19
<211> LENGTH: 414
<212> TYPE: DNA
<213> ORGANISM: Homo sapiens

<400> SEQUENCE: 19
atggacaggc ttacttcctc attcctgctg ctgattgtcc ctgcatatgt cctttcccag        60
gttactctga aagagtctgg ccctgggata ttgcagccct cccagaccct cagtctgact       120
tgttctttct ctgggttttc actgagcact tctggtatgg gtgtgagctg gattcgtcag       180
ccttcaggaa agggtctgga gtggctggca cacatttact gggatgatga caagcgctat       240 aaccccatccc tgaagagccg gctcacaatc tccaaggata cctccagaaa ccaggtattc       300
ctcaagatca ccagtgtgga cactgcagat actgccacat actactgtgc tcgaaaagga       360
gaaactgcgg ctatggacta ctggggtcaa ggaacctcag tcaccgtctc ctca            414

<210> SEQ ID NO 20
<211> LENGTH: 138
<212> TYPE: PRT
<213> ORGANISM: Homo sapiens

<400> SEQUENCE: 20

Met Asp Arg Leu Thr Ser Ser Phe Leu Leu Leu Ile Val Pro Ala Tyr
1               5                   10                  15

Val Leu Ser Gln Val Thr Leu Lys Glu Ser Gly Pro Gly Ile Leu Gln
            20                  25                  30

Pro Ser Gln Thr Leu Ser Leu Thr Cys Ser Phe Ser Gly Phe Ser Leu
        35                  40                  45

Ser Thr Ser Gly Met Gly Val Ser Trp Ile Arg Gln Pro Ser Gly Lys
    50                  55                  60

Gly Leu Glu Trp Leu Ala His Ile Tyr Trp Asp Asp Lys Arg Tyr
65                  70                  75                  80

Asn Pro Ser Leu Lys Ser Arg Leu Thr Ile Ser Lys Asp Thr Ser Arg
                85                  90                  95

Asn Gln Val Phe Leu Lys Ile Thr Ser Val Asp Thr Ala Asp Thr Ala
            100                 105                 110

Thr Tyr Tyr Cys Ala Arg Lys Gly Glu Thr Ala Ala Met Asp Tyr Trp
        115                 120                 125

Gly Gln Gly Thr Ser Val Thr Val Ser Ser
    130                 135

<210> SEQ ID NO 21
<211> LENGTH: 36
<212> TYPE: DNA
<213> ORGANISM: Homo sapiens

<400> SEQUENCE: 21
gggttttcac tgagcacttc tggtatgggt gtgagc                              36

<210> SEQ ID NO 22
<211> LENGTH: 12
<212> TYPE: PRT
<213> ORGANISM: Homo sapiens

<400> SEQUENCE: 22

Gly Phe Ser Leu Ser Thr Ser Gly Met Gly Val Ser
1               5                   10

<210> SEQ ID NO 23
<211> LENGTH: 48
<212> TYPE: DNA
<213> ORGANISM: Homo sapiens

<400> SEQUENCE: 23
cacatttact gggatgatga caagcgctat aacccatccc tgaagagc                 48

<210> SEQ ID NO 24
<211> LENGTH: 16
<212> TYPE: PRT
<213> ORGANISM: Homo sapiens

<400> SEQUENCE: 24

His Ile Tyr Trp Asp Asp Lys Arg Tyr Asn Pro Ser Leu Lys Ser
1               5                   10                  15

<210> SEQ ID NO 25
<211> LENGTH: 27
<212> TYPE: DNA
<213> ORGANISM: Homo sapiens

<400> SEQUENCE: 25
aaaggagaaa ctgcggctat ggactac                                         27

<210> SEQ ID NO 26
<211> LENGTH: 9
<212> TYPE: PRT
<213> ORGANISM: Homo sapiens

<400> SEQUENCE: 26

Lys Gly Glu Thr Ala Ala Met Asp Tyr
1               5

<210> SEQ ID NO 27
<211> LENGTH: 393
<212> TYPE: DNA
<213> ORGANISM: Homo sapiens

<400> SEQUENCE: 27
atggagacag acacactcct gttatgggta ctgctgctct gggttccagg ttccactggt      60
gacattgtgc tgacacagtc tcctgcttcc ttagctgtat ctctggggca gagggccacc     120
atctcatgca gggccagcaa aagtgtcagt acatctggct atatttttt gtactggtac      180 caacagaaac caggacagcc acccaaactc ctcatctatc ttgcatccaa cctagaatct     240
ggggtccctg ccaggttcag tggcagtggg tctgggacag acttcaccct caacatccat     300
cctgtggagg aggaggatgc tgcaacctat tactgtcagc acagtaggga gcttccgtgg     360
acgttcggtg aggcaccaa gctggaaatc aaa                                   393

<210> SEQ ID NO 28
<211> LENGTH: 131
<212> TYPE: PRT
<213> ORGANISM: Homo sapiens

<400> SEQUENCE: 28

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Lys Ser
            35                  40                  45

Val Ser Thr Ser Gly Tyr Ile Phe Leu Tyr Trp Tyr Gln Gln Lys Pro
        50                  55                  60

Gly Gln Pro Pro Lys Leu Leu Ile Tyr Leu Ala Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Asp Ala Ala Thr Tyr Tyr Cys
                100                 105                 110

Gln His Ser Arg Glu Leu Pro Trp Thr Phe Gly Gly Gly Thr Lys Leu
            115                 120                 125

Glu Ile Lys
        130

<210> SEQ ID NO 29

<211> LENGTH: 45
<212> TYPE: DNA
<213> ORGANISM: Homo sapiens

<400> SEQUENCE: 29

```
agggccagca aaagtgtcag tacatctggc tatatttttt tgtac            45
```

<210> SEQ ID NO 30
<211> LENGTH: 15
<212> TYPE: PRT
<213> ORGANISM: Homo sapiens

<400> SEQUENCE: 30

```
Arg Ala Ser Lys Ser Val Ser Thr Ser Gly Tyr Ile Phe Leu Tyr
1               5                   10                  15
```

<210> SEQ ID NO 31
<211> LENGTH: 21
<212> TYPE: DNA
<213> ORGANISM: Homo sapiens

<400> SEQUENCE: 31

```
cttgcatcca acctagaatc t                                       21
```

<210> SEQ ID NO 32
<211> LENGTH: 7
<212> TYPE: PRT
<213> ORGANISM: Homo sapiens

<400> SEQUENCE: 32

```
Leu Ala Ser Asn Leu Glu Ser
1               5
```

<210> SEQ ID NO 33
<211> LENGTH: 27
<212> TYPE: DNA
<213> ORGANISM: Homo sapiens

<400> SEQUENCE: 33

```
cagcacagta gggagcttcc gtggacg                                 27
```

<210> SEQ ID NO 34
<211> LENGTH: 9
<212> TYPE: PRT
<213> ORGANISM: Homo sapiens

<400> SEQUENCE: 34

```
Gln His Ser Arg Glu Leu Pro Trp Thr
1               5
```

<210> SEQ ID NO 35
<211> LENGTH: 1184
<212> TYPE: DNA
<213> ORGANISM: Homo sapiens

<400> SEQUENCE: 35

```
cgtgaggctc cggtgcccgt cagtgggcag agcgcacatc gcccacagtc cccgagaagt    60 tgggggagg ggtcggcaat tgaaccggtg cctagagaag gtggcgcggg gtaaactggg    120
aaagtgatgt cgtgtactgg ctccgccttt ttcccgaggg tgggggagaa ccgtatataa    180
gtgcagtagt cgccgtgaac gttctttttc gcaacgggtt tgccgccaga acacaggtaa    240
gtgccgtgtg tggttcccgc gggcctggcc tctttacggg ttatggccct tgcgtgcctt    300
```

-continued

```
gaattacttc cacctggctg cagtacgtga ttcttgatcc cgagcttcgg gttggaagtg      360
ggtgggagag ttcgaggcct tgcgcttaag gagccccttc gcctcgtgct tgagttgagg      420
cctggcctgg gcgctggggc cgccgcgtgc gaatctggtg gccccttcgc gcctgtctcg      480
ctgctttcga taagtctcta gccatttaaa attttgatg acctgctgcg acgctttttt       540
tctggcaaga tagtcttgta aatgcgggcc aagatctgca cactggtatt tcggttttg      600 gggccgcggg cggcgacggg gcccgtgcgt cccagcgcac atgttcggcg aggcggggcc      660
tgcgagcgcg gccaccgaga atcggacggg ggtagtctca agctggccgg cctgctctgg      720
tgcctggcct cgcgccgccg tgtatcgccc cgccctgggc ggcaaggctg cccggtcgg       780 caccagttgc gtgagcggaa agatggccgc ttcccggccc tgctgcaggg agctcaaaat      840
ggaggacgcg cgcgctcggga gagcgggcgg gtgagtcacc cacacaaagg aaaagggcct    900
ttccgtcctc agccgtcgct tcatgtgact ccacggagta ccgggcgccg tccaggcacc     960
tcgattagtt ctcgagcttt tggagtacgt cgtctttagg ttggggggag gggttttatg    1020
cgatggagtt tccccacact gagtgggtgg agactgaagt taggccagct tggcacttga    1080
tgtaattctc cttggaattt gccctttttg agtttggatc ttggttcatt ctcaagcctc    1140
agacagtggt tcaaagtttt tttcttccat ttcaggtgtc gtga                     1184
```

<210> SEQ ID NO 36
<211> LENGTH: 63
<212> TYPE: DNA
<213> ORGANISM: Homo sapiens

<400> SEQUENCE: 36

```
atggccctgc ctgtgacagc cctgctgctg cctctggctc tgctgctgca tgccgctaga       60
ccc                                                                    63
```

<210> SEQ ID NO 37
<211> LENGTH: 21
<212> TYPE: PRT
<213> ORGANISM: Homo sapiens

<400> SEQUENCE: 37

Met Ala Leu Pro Val Thr Ala Leu Leu Leu Pro Leu Ala Leu Leu Leu
1               5                   10                  15

His Ala Ala Arg Pro
            20

<210> SEQ ID NO 38
<211> LENGTH: 336
<212> TYPE: DNA
<213> ORGANISM: Homo sapiens

<400> SEQUENCE: 38

```
gatattgtta tgacgcaagc agcacctagc gtactcgtaa ctcctggaga gagcgtgtct       60
atttcatgtc ggtcttctaa aagtctcctt tacggtaacg ggaatactta cctttactgg      120
ttcctgcaga ggcccggcca gtccccacag cttctcattt atagaatgag taacctcgct      180 tcagggtcc cagaccgatt cagcgggtca ggctccggta ccgccttcac tttgcggatt      240
agccgggtgg aagcggaaga cgttggggta tattactgta tgcagcatct tgaataccccc     300 cttacctttg gtgccggaac aaaattggaa ctcaaa                                336
```

<210> SEQ ID NO 39
<211> LENGTH: 333

<212> TYPE: DNA
<213> ORGANISM: Homo sapiens

<400> SEQUENCE: 39

```
gacatcgtct tgacccagtc tccggcaagt ctggcggtct cacttgggca aagagcgaca      60
atttcatgcc gcgcatcaaa aagtgtctca acgtctggct atatattcct ttactggtac     120
caacaaaagc cggggcaacc ccccaaactg ctcatctacc ttgcatctaa tttggaatcc     180
ggggttccag cgagatttag tgggagtggt agtggcaccg attttactct gaatatccat     240
cctgttgagg aggaagatgc tgccacgtac tattgccaac attcaaggga gttgccgtgg     300
acctttggag gtggaaccaa gttggagatc aaa                                  333
```

<210> SEQ ID NO 40
<211> LENGTH: 30
<212> TYPE: DNA
<213> ORGANISM: Homo sapiens

<400> SEQUENCE: 40

```
ggtggcggag gttctggagg tggaggttcc                                       30
```

<210> SEQ ID NO 41
<211> LENGTH: 10
<212> TYPE: PRT
<213> ORGANISM: Homo sapiens

<400> SEQUENCE: 41

```
Gly Gly Gly Gly Ser Gly Gly Gly Gly Ser
1               5                   10
```

<210> SEQ ID NO 42
<211> LENGTH: 360
<212> TYPE: DNA
<213> ORGANISM: Homo sapiens

<400> SEQUENCE: 42

```
cagatccagt tggtccaatc aggcccagag ctgaagaagc ccggtgagac ggttaagatt      60
agttgtaaag cgagcggcta cacttttact aattcaggta tgaattgggt aaaacaagca     120
ccagggaaag gactgaaatg gatgggatgg atcaatacct acaccggaga gccaacttac     180
gctgacgact tcaaagggag gttcgccttc agcctgaaaa caagtgcttc caccgcgtac     240
ctccagatca ataacctgaa gaatgaagat acggctacgt acttctgcgt gcgggcagga     300
tcttatcgaa actacgcaat ggattactgg ggccagggta caagtgtgac ggtatcatca     360
```

<210> SEQ ID NO 43
<211> LENGTH: 357
<212> TYPE: DNA
<213> ORGANISM: Homo sapiens

<400> SEQUENCE: 43

```
caggttactc tcaaggagtc cggtcctggg atactccagc caagtcagac actgtccctt      60
acgtgcagct tttcaggctt ttcattgagt acatctggaa tgggcgtgag ttggatacgg     120
caaccttctg gaagggggct cgaatggctg gcccatattt attgggatga tgataaagaa     180
tacaacccct ctctcaagag taggttgact atcagcaagg atacctcacg gaatcaagtg     240
tttctgaaga ttacgtcagt ggatacggca gatacagcaa cgtactactg cgccagaaaa     300
ggtgagacag cagcgatgga ctattgggga cagggcacgt ctgtgacagt gtcatca       357
```

```
<210> SEQ ID NO 44
<211> LENGTH: 135
<212> TYPE: DNA
<213> ORGANISM: Homo sapiens

<400> SEQUENCE: 44
accacgacgc cagcgccgcg accaccaaca ccggcgccca ccatcgcgtc gcagcccctg    60
tccctgcgcc agaggcgtg ccggccagcg gcggggggcg cagtgcacac gaggggctg    120 gacttcgcct gtgat                                                   135

<210> SEQ ID NO 45
<211> LENGTH: 45
<212> TYPE: PRT
<213> ORGANISM: Homo sapiens

<400> SEQUENCE: 45

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 46
<211> LENGTH: 72
<212> TYPE: DNA
<213> ORGANISM: Homo sapiens

<400> SEQUENCE: 46
atctacatct gggcgccctt ggccgggact tgtggggtcc ttctcctgtc actggttatc    60 acccttact gc                                                        72

<210> SEQ ID NO 47
<211> LENGTH: 24
<212> TYPE: PRT
<213> ORGANISM: Homo sapiens

<400> SEQUENCE: 47

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 48
<211> LENGTH: 123
<212> TYPE: DNA
<213> ORGANISM: Homo sapiens

<400> SEQUENCE: 48
aggagtaaga ggagcaggct cctgcacagt gactacatga acatgactcc ccgccgcccc    60
gggcccaccc gcaagcatta ccagccctat gccccaccac gcgacttcgc agcctatcgc    120
tcc                                                                 123

<210> SEQ ID NO 49
<211> LENGTH: 48
<212> TYPE: PRT
<213> ORGANISM: Homo sapiens

<400> SEQUENCE: 49

Gln Arg Arg Lys Tyr Arg Ser Asn Lys Gly Glu Ser Pro Val Glu Pro
```

```
                1               5                  10                  15
Ala Glu Pro Cys Arg Tyr Ser Cys Pro Arg Glu Glu Glu Gly Ser Thr
                20                  25                  30

Ile Pro Ile Gln Glu Asp Tyr Arg Lys Pro Glu Pro Ala Cys Ser Pro
                35                  40                  45
```

<210> SEQ ID NO 50
<211> LENGTH: 30
<212> TYPE: DNA
<213> ORGANISM: Homo sapiens

<400> SEQUENCE: 50
ggtggcggag gttctggagg tggaggttcc                                      30

<210> SEQ ID NO 51
<211> LENGTH: 10
<212> TYPE: PRT
<213> ORGANISM: Homo sapiens

<400> SEQUENCE: 51

```
Gly Gly Gly Gly Ser Gly Gly Gly Gly Ser
1               5                  10
```

<210> SEQ ID NO 52
<211> LENGTH: 126
<212> TYPE: DNA
<213> ORGANISM: Homo sapiens

<400> SEQUENCE: 52
aaacggggca gaaagaaact cctgtatata ttcaaacaac catttatgag accagtacaa     60
actactcaag aggaagatgg ctgtagctgc cgatttccag aagaagaaga aggaggatgt    120
gaactg                                                               126

<210> SEQ ID NO 53
<211> LENGTH: 42
<212> TYPE: PRT
<213> ORGANISM: Homo sapiens

<400> SEQUENCE: 53

```
Lys Arg Gly Arg Lys Lys Leu Leu Tyr Ile Phe Lys Gln Pro Phe Met
1               5                  10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
                35                  40
```

<210> SEQ ID NO 54
<211> LENGTH: 30
<212> TYPE: DNA
<213> ORGANISM: Homo sapiens

<400> SEQUENCE: 54
ggtggcggag gttctggagg tggaggttcc                                      30

<210> SEQ ID NO 55
<211> LENGTH: 10
<212> TYPE: PRT
<213> ORGANISM: Homo sapiens

<400> SEQUENCE: 55

Gly Gly Gly Gly Ser Gly Gly Gly Gly Ser

<210> SEQ ID NO 56
<211> LENGTH: 336
<212> TYPE: DNA
<213> ORGANISM: Homo sapiens

<400> SEQUENCE: 56

```
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
cgggaccctg agatggggggg aaagccgaga aggaagaacc ctcaggaagg cctgtacaat    180
gaactgcaga aagataagat ggcggaggcc tacagtgaga ttgggatgaa aggcgagcgc     240
cggaggggca aggggcacga tggcctttac cagggtctca gtacagccac caaggacacc     300
tacgacgccc ttcacatgca ggccctgccc cctcgc                                336
```

<210> SEQ ID NO 57
<211> LENGTH: 112
<212> TYPE: PRT
<213> ORGANISM: Homo sapiens

<400> SEQUENCE: 57

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 58
<211> LENGTH: 20
<212> TYPE: DNA
<213> ORGANISM: Homo sapiens

<400> SEQUENCE: 58

```
gagtggctgg cacacatcta                                                   20
```

<210> SEQ ID NO 59
<211> LENGTH: 20
<212> TYPE: DNA
<213> ORGANISM: Homo sapiens

<400> SEQUENCE: 59

```
aggagaagga ccccacaagt                                                   20
```

CHIMERIC ANTIGEN RECEPTOR SPECIFIC TO B-CELL MATURATION ANTIGEN, A RECOMBINANT EXPRESSION VECTOR AND A METHOD THEREOF

CROSS REFERENCE TO RELATED APPLICATIONS

This patent application is a national stage filing under 35 U.S.C. § 371 of International Application No. PCT/IN2017/050040, filed on Jan. 28, 2017, published as WO 2017130223 on Aug. 3, 2017, and claims the benefit of Indian Provisional Patent Application No. 201641003422, filed Jan. 29, 2016, the entire disclosures of which are incorporated by reference in their entireties herein.

REFERENCE TO A SEQUENCE LISTING SUBMITTED VIA EFS-WEB

The content of the ASCII text file of the Sequence Listing named "2020-07-31 Updated-Sequence-Listing 108789-0006.txt" which was created on Jul. 30, 2020; and is 24,576 bytes in size, submitted electronically via EFS-Web in this U.S. patent application is hereby incorporated by reference in its entirety into the instant application.

FIELD OF INVENTION

The present invention relates to a chimeric antigen receptors specific to B-cell maturation antigen, a recombinant expression vector and a method thereof, and more particularly relates to the generation of genetically immune effector cells especially natural killer cells (NK cells) natural killer-92 cells (NK-92 cells), human T lymphocytes (T cells) and natural killer T cells (NKT cells) and various fractions of hematopoietic stem cells with third-generation chimeric antigen receptors (CARs) comprising of a single-chain variable fragment (scFv) of monoclonal antibodies (mAb) specific to B-cell maturation antigen (BCMA) which redirects immune effector cell specificity and reactivity toward including but not limited to multiple myeloma cancer cells expressing the BCMA for a new and improved adoptive cellular immunotherapy.

BACKGROUND OF THE INVENTION

Multiple myeloma (MM) is a hematologic malignancy characterized by accumulation of clonal plasma cells in bone marrow often associated with bone lesions. Although hematopoietic stem cell transplantation along with newer drugs such as thalidomide and proteasome inhibitors often induces an initial remission, however, the tumor relapse due to chemoresistance remains a major problem. The immune system can detect and eliminate tumor cells by activation T lymphocytes (T cells), and harnessing a patient's own immune system has become an increasingly attractive therapeutic option. The presence of tumor-reactive T cells in peripheral blood of cancer patients has given rise to the concept of adoptive cell therapy (ACT).

The ACT is the process by which immune effector cells, in general T cells, transferred to a patient that are capable of homing to tumor sites throughout the body and induce an antitumor effect. Ex vivo expansion and reinfusing of tumor-infiltrating lymphocytes (TILs) back into patients has yielded clinical successes in many cases fostering considerable optimism of T cell based ACT. Despite promising clinical efficiency of T cell therapies, its widespread applicability is limited by several factors. Tumor lysis of T cells require recognition of tumor antigens presented in the context of human leukocyte antigen (HLA) class I or II by a specific T-cell receptor (TCR). One of the major immune escape mechanisms of tumors is down regulation of the HLA molecules apart from inhibiting various aspects of T cell functions. Further adoptive T cell therapies face a hostile tumor-microenvironment induced by tumors to escape recognition thus making T cell therapy less effective. Tumors and surrounding stroma often acquire a multiplicity of means to evade immune surveillance and subvert the immune system by activating immunosuppressive pathways. Further tumor-induced immunosuppression inhibits T cell maturation and their ability of migration to tumor site to induce cancer cell death. Therefore, overcoming HLA restriction and/or tumor-induced immunosuppression is required for successful T cell therapy.

Chimeric antigen receptor (CAR) technologies are designed not only to mitigate general immunosuppressive tumor microenvironment but also redirecting of immune effector cells to HLA-independent recognition of cell surface tumor specific antigens. CARs are artificially generated for expression on immune effector cells as trans-membrane receptors to identify tumor cell surface Antigen. They also belong to the class of ACT, where immunological effector cells are harvested, their immunological activity is genetically modified ex vivo targeting cancer cell specific surface Antigen, expanded and then reinfused into the same host to kill the cancer cells. CARs thus effectively integrate principles of T cell recognition of tumor antigen without HLA restriction. Hence CAR-T cell mediated therapy is applicable to all patients irrespective of their HLA haplotype thus overcoming major immune escape mechanisms of tumors such as down-regulation of HLA molecules.

Identification of MM specific cell surface Antigen followed by the development of mAb for said Antigen is the essential primary step for the development of CAR-T cell mediated therapy. Recent studies indicated the development of CARs targeting multiple myeloma specific cell surface antigens such as CD138 [1] and CS-1 [2, 3] with potential antitumor activity. Intravenous infusion of multiple myeloma patients with CAR-T cells targeting CD138 showed in vivo expansion over 1000 times with reduction of myeloma cells. Similarly, CAR-NK cells targeting cells displayed enhanced cytotoxicity of primary myeloma cells and inhibited growth of orthotopic xenografts in mouse model.

BCMA is another more promising CAR target for multiple myeloma because it is an essential membrane protein for maintaining the survival of malignant plasma cells. BCMA is a 27 kDa, single pass transmembrane protein, also known as tumor necrosis factor receptor superfamily member 17 (TNFRSF17) and cluster of differentiation 269 antigen (CD269). The ligands of CD269 are BAFF and APRIL, and its cytoplasmic domain binds several of the TRAF family members. It is expressed by, plasma cells, and germinal center B cells but is absent on naive B cells and on most memory B cells and is essential for the long-term survival of plasma cells. Upon stimulation by a proliferation inducing ligand (APRIL) or B-cell-activating factor (BAFF), BCMA is internalized with subsequent induction of anti-apoptotic proteins. Further, therapeutic anti-BCMA antibodies have shown promising in vitro activity against multiple myeloma cell lines and primary patient samples indicating said Antigen is ideal target for CAR-T cell mediated therapy.

In fact CAR-T cells targeting BCMA using immune effector T cells with different scFv have demonstrated significant killing of cell lines and primary multiple myeloma cells. [4, 5, 6, 7] A potential limitation of this method of using effector T cells for CAR mediated therapy is the need for customized expansion of effector T cells harvested by leukapheresis either from the same patient (autologous transplant) or from donor (allogeneic transplant) followed by genetic modification introducing CARs, expanding and manufacturing. Leukapheresis is a process where white blood cells are removed to protect them from damage before high-dose chemotherapy, then transfused back into the patient. Often patients require immediate therapy and generation of CAR-T cells for adoptive cell therapy, is ill suited as the manufacturing processes require several weeks starting with leukapheresis in case of autologous transplant. Allogeneic transplantation needs careful HLA to overcome Graft-versus-host disease (GvHD), too long for a patient with active malignancy. GvHD is a common side effect of an allogeneic bone marrow transplant and occurs because of differences in the expression of various Antigens between recipient and donor, the most important being the expression of various HLA molecules. Even with high resolution molecular typing of HLA molecules, the degree of acceptability matching donor to recipient is open for debate and the search for a completely matched donor may take time, too long for a patient with active malignancy. To overcome complications related to GvHD related to HLA restriction and/or tumor-induced immunosuppression, NK cells are increasingly considered instead of T cells.

NK cells are critical component of the innate immune response and important players in the first line of defense against malignant cells. Ability of NK cells to kill malignant cells without prior sensitization contributes to its rapid action unlike T cells, which require recognition of tumor antigens presented in the context of HLA molecules. Clinical efficacy of primary NK cells will however remain variable due to individual differences. Further, long-term storage of NK cells for repeated clinical applications remains an additional challenge.

Therefore, the problem to be solved is to provide an approach to overcome variability due to individual differences, long term storage for repeated clinical applications and other problems as stated above, and the problem is solved by providing a novel approach as in present invention different from cell therapy with endogenous NK cells of host (autologous) or donor (allogeneic) origin involves the permanent IL-2 dependent NK cell line, NK-92 with a novel CAR protein that comprises a binding domain directed against BCMA, a transmembrane domain, an intracellular co-stimulatory signaling domain and an intracellular activation domain in which the BCMA binding domain is an isolated nucleic acid encoding anti-BCMA antibody with a variable heavy ($V_H$) domain and a variable light ($V_L$) domain connected by a peptide linker sequence of SEQ ID NO: 23 constituting a single-chain Fragment variable (scFv) domain, thereby further increasing immune effector cell function.

SUMMARY OF THE INVENTION

An embodiment of the present invention discloses a chimeric antigen receptors (CARs) specific to B-cell maturation antigen (BCMA), also known as tumor necrosis factor receptor superfamily member 17 (TNFRSF17) and CD269 antigen (CD269), a recombinant expression vector and a method thereof for the development of the genetically modified immune effector cells especially natural killer cells (NK cells) natural killer-92 cells (NK-92 cells), human T lymphocytes (T cells) and natural killer T cells (NKT cells) and various fractions of hematopoietic stem cells derived from cord blood, bone marrow or peripheral blood with CARs comprising of a single-chain variable fragment (scFv) of the variable regions of the heavy ($V_H$) and light chain ($V_L$) of an antibody specific to BCMA. CARs are trans-membrane proteins comprising of single chain antibody, a hinge domain; a trans-membrane domain, an intracellular signaling domain derived from human CD3-ζ and one or more stimulatory signaling domains CD28 and 4-1BB that can further increase immune effector cell function, wherein the BCMA binding domain is an isolated nucleic acid encoding anti-BCMA antibody with a variable heavy ($V_H$) domain and a variable light ($V_L$) domain connected by a peptide linker SEQ ID NO: 40, SEQ ID NO: 41 constituting a single-chain Fragment variable (scFv) domain.

A major advantage of permanent NK cell lines such as NK-92 is the ease of their maintenance and expansion in culture. Leukapheresis is unnecessary, which avoids potential adverse effects. NK-92 cell line has been well documented in vitro for antitumor activity and has been approved by the Food and Drug Administration for clinical testing in patients. It is currently the only NK cell line to date that has entered clinical trials. Furthermore, the product can be made available in large quantities at high purity with reproducible characteristics. NK-92 can be easily expanded in cultures to generate potent clinical-grade NK-92 effectors, thus, applicable as an off-the-shelf product to any patient unlike T cells. There have been several successful clinical trials of adoptively transferred allogeneic NK cells and NK-92 cells for multiple myeloma immunotherapy.

The potential benefit of the NK cell lines is their inability to be inhibited by recipient human leukocyte antigen (HLA) because of low expression of KIRs or KIR-HLA mismatch in the recipient. Established and well-characterized NK cell lines can be easily and reproducibly expanded from a good manufacturing practice (GMP)-compliant cryopreserved master cell bank without having to establish purification methods.

Further, CARs expressed on immune effector cells initiate target cell killing by activating various apoptosis inducing signaling pathways following binding to BCMA expressed on the MM cells.

According to an embodiment of the invention, the transmembrane domain and the scFv domains are connected by a hinge domain, wherein said hinge domain is derived from CD8-α with SEQ ID NO: 44, 45.

According to an embodiment of the invention, the $V_H$ domain, includes a murine SEQ ID NO: 3, 4; SEQ ID NO: 19, 20.

According to an embodiment of the invention, the $V_H$ domain possessing complementarity-determining regions (CDRs) comprises of a $V_H$ CDR1 sequences of SEQ ID NO:5, 6; SEQ ID NO:21, 22; a $V_H$ CDR2 sequences of SEQ ID NO:7, 8; and SEQ ID NO:23, 24; and a $V_H$ CDR3 sequences of SEQ ID NO:9, 10; and SEQ ID NO: 25, 26.

According to an embodiment of the invention, the $V_H$ domain includes a human codon optimized SEQ ID NO: 42 and SEQ ID NO: 43.

According to an embodiment of the invention, the $V_L$ domain includes a murine SEQ ID NO: 11, 12 and SEQ ID NO: 27, 28

According to an embodiment of the invention, the $V_L$ domain possessing complementarity-determining regions (CDRs) comprises of a $V_L$ CDR1 sequences of SEQ ID NO:

13, 14 and SEQ ID NO: 29, 30; a $V_L$ CDR2 sequences of SEQ ID NO:15, 16 and SEQ ID NO:31, 32 and a $V_L$ CDR3 sequences of SEQ ID NO:17, 18 and SEQ ID NO:33, 34.

According to an embodiment of the invention, the $V_L$ domain, includes a human codon optimized SEQ ID NO: 38, 39.

According to an embodiment of the invention, the transmembrane domain can be any of the functional signaling domains selected from the group consisting of the T cell receptor, CD28, CD3 CD45, CD8 and CD16.

According to an embodiment of the invention, the transmembrane domain comprises a sequence of SEQ ID NO: 46, 47.

According to an embodiment of the invention, the intracellular co-stimulatory domains can be any of the functional signaling domain selected from the group consisting of OX40, CD27, CD28, ICAM-1, ICOS (CD278), and 4-1BB (CD137).

According to an embodiment of the invention, the intracellular co-stimulatory domains comprise SEQ ID NO: 48, 49 and SEQ ID NO: 52, 53.

According to an embodiment of the invention, the intracellular activation domain can be CD3-ζ with a sequence of SEQ ID NO: 56, 57.

According to an embodiment of the invention, a recombinant expression vector comprising said isolated nucleic acid as claimed in any one of the preceding claims, wherein said recombinant expression vector is selected from the group consisting of a DNA, a RNA, a plasmid, a lentivirus vector or adeno-associated viral vector.

According to an embodiment of the invention, the recombinant expression vector comprises EF-1α promoter of SEQ ID NO: 35

According to an embodiment of the invention, a method for generation of a chimeric antigen receptors (CARs) specific to B-cell maturation antigen (BCMA) including transducing cells with said B-cell maturation antigen (BCMA) specific a chimeric antigen receptor (CAR) vector to generate genetically engineered cells, wherein said genetically engineered cells are selected from the group consisting of human T lymphocytes, natural killer cells (NK cells), NK-92 cells, and natural killer T cells (NKT cells).

According to an embodiment of the invention, the method includes administering cells to subject with multiple myeloma, other hematological malignancies and any precancerous conditions, wherein at least a subpopulation of the cells of said cancer expresses BCMA.

According to an embodiment of the invention, the cells expressing a CAR are administered in combination with chemotherapeutic agent that ameliorates side effects and increase therapeutic benefit.

BRIEF DESCRIPTION OF DRAWINGS

FIG. 2A. Agarose gel electrophoresis of total RNA from the hybridoma of the clone 1E1E. The isolated total RNA of the sample was run alongside a DNA marker (Marker III, TIANGEN Biotech Cat. No.: MD103) on a 1.5% agarose/ Gel. Lane M: DNA marker III; Lane Total ribosomal RNA (rRNA) 28S rRNA (top band), 8S rRNA (middle band), 5S rRNA (bottom band). FIG. 2B. Agarose gel electrophoresis of antibody genes PCR products of the BCMA CAR clone 1E1E. Four microliters of PCR products of each sample were run alongside the DNA marker (Marker III, TIANGEN Biotech Cat. No.: MD103) on a 1.5% agarose. Lane M: DNA Marker III; Lane $V_H$: PCR product of variable heavy chain, Lane $V_L$: PCR product of variable light chain.

FIG. 3A. Agarose gel electrophoresis of total RNA from the hybridoma of the BCMA CAR clone 2D4A. The isolated total RNA of the sample was run alongside a DNA marker (Marker III, TIANGEN Biotech Cat. No.: MD103) on a 1.5% agarose/Gel. Lane M: DNA marker III; Lane Total ribosomal RNA (rRNA) 28S rRNA (top hand), 8S rRNA (middle hand), 5S rRNA (bottom hand). FIG. 3B. Agarose gel electrophoresis of antibody genes PCR products of the BCMA CAR clone 2D4A. Four microliters of PCR products of each sample were run alongside the DNA marker (Marker III, TIANGEN Biotech Cat. No.: MD103) on a 1.5% agarose. Lane M: DNA Marker III; Lane $V_H$: PCR product of variable heavy chain, Lane $V_L$: PCR product of variable light chain.

FIG. 5A. SDS-PAGE analysis of antigen-binding domain of the BCMA CAR clone 1E1E monoclonal antibody. Lane M: Protein marker, Lane 1: Reducing conditions, Lane 2: Non-reducing conditions. FIG. 5B. Western blot analysis antigen-binding domain of the BCMA CAR clone 1E1E monoclonal antibody. Anti-Human IgG(H&L)(GOAT) primary antibody (ROCKLAND, Cat. No. 609-132-123) was used as primary antibody for detection. Lane M: Protein marker, Lane P: Human IgG1, Kappa (Sigma, Cat. No. I5154) as positive control; Lane 1: Reducing conditions, Lane 2: Non-reducing conditions.

L00433). FIG. 6A. SDS-PAGE analysis of antigen-binding domain of the BCMA CAR clone 2D4A monoclonal antibodies. Lane M: Protein marker, Lane 1: Reducing conditions, Lane 2: Non-reducing conditions. FIG. 6B. Western blot analysis antigen-binding domain of the DCMA CAR clone 2D4A monoclonal antibodies. Anti-Human IgG(II&L) (GOAT) primary antibody (ROCKLAND, Cat. No. 609-132-123) was used as primary antibody for detection. Lane M: Protein marker, Lane P: Human IgG1, Kappa (Sigma, Cat. No. I5154) as positive control; Lane 1: Reducing conditions, Lane 2: Non-reducing conditions.

DETAILED DESCRIPTION OF INVENTION

Figure 1:
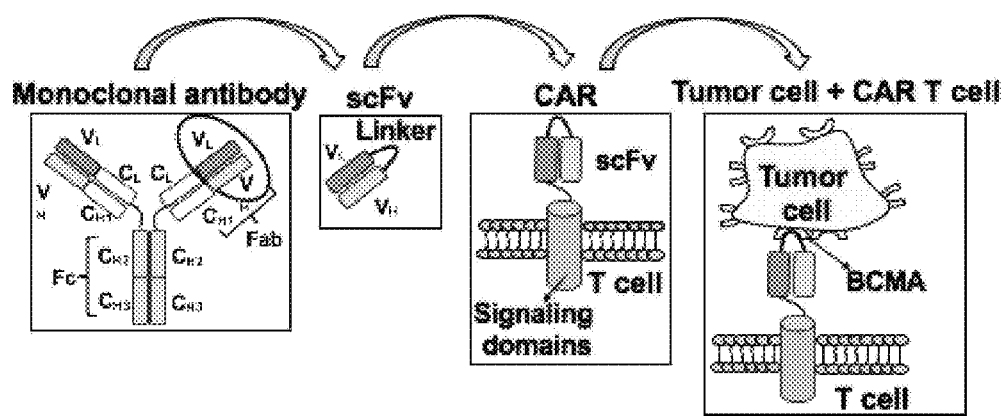
FIG. 1 discloses schematic representation of the single-chain fragment variable (scFv) of BCMA fragments encoding variable regions of heavy ($V_H$) and light ($V_L$) chains connected by a linker. Toward the end, scFv is connected to signaling domain (encompassing CD28, spanning the transmembrane and cytoplasmic regions with 4-1BB co-stimulatory and CD3ζ activation domains). Diagram also discloses engraftment of BCMA CAR onto T cells and tumor cell killing via BCMA-CAR T cell binding to tumor cell surface.

The embodiments of the present invention can be understood by reading following detailed description of some of the embodiments with reference to the accompanying drawings.

In an embodiment of the present invention, a chimeric antigen receptor (CAR) comprising an extra-cellular B-cell maturation antigen (BCMA) binding domain is disclosed for the treatment of various hematological malignancies including multiple myeloma. The BCMA protein is expressed on a cancer cell. The antigen-binding portion of the CAR interacts with an epitope within the extracellular domain of the BCMA fragment thereof.

As used herein the term "antibody", refers to a polypeptide sequence derived from an immunoglobulin molecule, which specifically binds with BCMA antigen. As used herein the term "Antigen' refers to a molecule that provokes an immune response and virtually all proteins or peptides, can serve as an Antigen. As used herein the term "peptide linker' in the context of a scFv refers to a peptide linker that consists of amino acids to link variable heavy and variable light chain regions together.

As used herein the phrase "immune effector cell" include human T lymphocytes, natural killer (NK) cells, natural killer T (NKT), and NK-92 cells.

As used herein the phrase "effector function" refers to a specialized function of a cell. Effector function of a T cell, for example, may be cytotoxic activity or helper activity including the secretion of cytokines. Immune effector response as that term is used herein, refers to enhanced immune attack of a target cancer cell. The term "cancer" refers to a disease characterized by the rapid and uncontrolled growth of aberrant cells. Cancer cells can spread locally or through the bloodstream and lymphatic system to other parts of the body. Examples of various hematological malignancies described herein include but are not limited to, multiple myeloma. The terms "tumor" and "cancer" are used interchangeably and includes premalignant, as well as malignant cancers and tumors.

As used herein the term "antigen recognition domain" refers to a portion of an antibody, and refers scFv comprising variable region of a heavy chain domain that is $V_H$ and another antibody portion comprising a variable region of a light domain that is $V_L$ wherein both the domains are connected by a linker set forth by DNA SEQ ID NO: 40 and amino acid SEQ ID NO: 41. The CAR is a chimeric fusion protein comprising an extracellular BCMA binding domain (scFv), a transmembrane domain, two intracellular co-stimulatory signaling domains and one intracellular activation domain.

The transmembrane domain and the scFv domains are connected by a hinge domain, which is derived from CD8-α. Hinge domain DNA sequence of CD8-α is set forth by SEQ ID NO: 44 and amino acid sequence is set forth by SEQ ID NO: 45. The transmembrane domain can be selected from any of the functional signaling domains selected from the group consisting of the T cell receptor, CD28, CD3-ζ CD45, CD8 and CD16. Further, in one aspect, transmembrane domain is also derived from CD8-α wherein the DNA sequence is set forth by SEQ ID NO: 46 and amino acid sequence is set forth by SEQ ID NO: 47.

First intracellular co-stimulatory domain can be any of the functional signaling domain selected from the group consisting of OX40, CD27, ICOS (CD278), ICAM-1 or CD28.

Second intracellular co-stimulatory domain comprising sequences of 4-1BB (CD137) refers to a member of the TNFR superfamily.

The intracellular activation domain is CD3-ζ, whose DNA sequence is set forth by SEQ ID NO: 56 and CD3-ζ amino acid sequence is set forth by SEQ ID NO: 57.

The linker sequence connecting CD27 and 4-1BB is set forth by SEQ ID NO: 50, 51.

The first intracellular co-stimulatory domain, CD27 is set forth by a DNA sequence of SEQ ID NO: 48 and amino acid sequence is set forth by SEQ ID NO: 49. The second intracellular co-stimulatory domain, 4-1BB DNA sequences set forth by SEQ ID NO: 52 and amino acid sequence set forth by SEQ ID NO: 53.

The co-stimulatory molecules act by transmitting information within the immune effector cell by generating second messenger signaling that promotes activities to kill the cancer cells. The CAR used herein comprises an Antigen binding domain scFv that binds a specific tumor marker BCMA. Immune effector cells especially NK cells, NK-92 cells, human T lymphocytes, and NKT cells are engineered to express a chimeric antigen receptor (CAR), wherein the cell (e.g., CAR-expressing immune effector cell, e.g., CAR-T cell) exhibits an antitumor property with a preferred antigen BCMA.

Further, the complementarity determining region (CDR), refers to the sequences of amino acids within antibody variable regions which confer antigen specificity and binding affinity. For example, in general, there are three CDRs in each variable heavy ($V_H$) domain and three CDRs in each variable light ($V_L$) domain. The $V_H$ domain is possessing complementarity-determining regions (CDRs) comprising, a $V_H$ CDR1 sequences of SEQ ID NO: 5, 6 (CDR1 heavy chain variable region ($V_H$) sequence (Clone #1E10E4 cell line)) and SEQ ID NO: 21, 22 (CDR1 heavy chain variable region ($V_H$) sequence (Clone #2D4A8 cell line)), a $V_H$ CDR2 sequences of SEQ ID NO: 7, 8 (CDR2 heavy chain variable region ($V_H$) sequence (Clone #1E10E4 cell line)) and SEQ ID NO: 23, 24 (CDR2 heavy chain variable region ($V_H$) sequence (Clone #2D4A8 cell line)); and a $V_H$ CDR3 sequences of SEQ ID NO: 9, 10 (CDR3 heavy chain variable region ($V_H$) sequence (Clone #1E10E4 cell line)) and SEQ ID NO: 25, 26 (CDR3 heavy chain variable region ($V_H$) sequence (Clone #2D4A8 cell line)).

The ($V_H$) domain also includes a human codon optimized DNA sequences of SEQ ID NO: 42, 43 (Human codon optimized $V_H$ DNA sequences (Clone #1E10E4 cell line)). The $V_H$ domain also include murine sequences of SEQ ID NO: 3, 4 (Heavy chain variable region ($V_H$) sequences (Clone #1E10E4 cell line)) and SEQ ID NO: 19, 20 (Heavy chain variable region ($V_H$) sequences (Clone #2D4A8 cell line)).

The $V_L$ domain possessing complementarity-determining regions (CDRs) comprises of, a $V_L$ CDR1 sequences of SEQ ID NO: 13, 14 (CDR1 light chain variable region ($V_L$) sequences (Clone #1E10E4 cell line)) and SEQ ID NO: 21, 22 (CDR1 light chain variable region ($V_L$) sequences (Clone #2D4A8 cell line)), a $V_L$ CDR2 sequences of SEQ ID NO: 15, 16 (CDR2 light chain variable region ($V_L$) sequences (Clone #1E10E4 cell line)) and SEQ ID NO: 23, 24 (CDR2 light chain variable region ($V_L$) sequences (Clone #2D4A8 cell line) and a $V_L$ CDR3 sequences of SEQ ID NO: 17, 18 (CDR3 light chain variable region ($V_L$) sequences (Clone #1E10E4 cell line)) and SEQ ID NO: 25, 26 (CDR3 light chain variable region ($V_L$) sequences (Clone #2D4A8 cell line)). The $V_L$ domain, also includes a human codon optimized DNA sequences of SEQ ID NO: 38, 39 (Human codon optimized $V_L$ DNA sequence (Clone #1E10E4 cell line)).

Further, the anti-BCMA binding domain, e.g., human scFv, portion of a CAR of the invention is encoded by a transgene whose sequence has been codon optimized for expression in a mammalian cell. The entire CAR construct of the invention is encoded by a transgene whose sequence has been codon optimized for expression in a mammalian cell. Codon optimization refers to the discovery that the frequency of occurrence of synonymous codons (i.e., codons that code for the same amino acid) in coding DNA is biased in different species. Such codon degeneracy allows an identical polypeptide to be encoded by a variety of nucleotide sequences.

The immune effector cells are transduced with a lentiviral vector encoding a CAR and cells may stably express the CAR. The immune effector cells are transfected with a nucleic acid encoding a CAR in that case the cell may transiently express the CAR.

The humanized antibodies are chimeric immunoglobulins, thereof, which contain minimal sequence derived from non-human immunoglobulin. For the most part, humanized antibodies and antibody fragments thereof are human immunoglobulins (recipient antibody or antibody fragment) in which residues from a CDR of the recipient are replaced by residues from a CDR of a non-human species (donor antibody) such as mouse. The humanized antibody or antibody fragment can also comprise at least a portion of an immunoglobulin constant region (Fc), typically that of a human immunoglobulin.

Skilled artisan would know that the "expression" is an inherent property of specific sequences of nucleotides in a polynucleotide, such as a gene which serves as templates for synthesis of messenger RNA (mRNA) resulting protein synthesis therefrom which would be known to one skilled in the art. As used herein the term "expression' refers to the transcription and/or translation of gene driven by the promoter. An expression vector comprises sufficient cis-acting elements for expression; other elements for expression can be supplied by the host cell or in an in vitro expression system.

As used herein the term "promoter" refers to a DNA sequence recognized by the nuclear transcriptome that would initiate the specific transcription of a gene. This may be the core promoter and may also include an enhancer sequence and other regulatory elements that constitute transcriptome. The promoter and regulatory sequences may express the gene product in a tissue specific manner.

In order to enhance immunogenicity, selected BCMA peptide (SEQ ID NO: 1) (Sequence of Antigen) that is surface exposed was further added with Cysteine and Proline amino acid residues at N terminal end (SEQ ID NO: 2) (Modified sequence of Antigen). Although, addition of these amino acids increases immunogenicity, peptides by themselves in general are weak immunogens to evoke antibody response. Further, SEQ ID NO: 2 was conjugated to keyhole limpet hemocyanin (KLH), a known stimulator of T-helper cells (Th). Though solubility of KLH in water is limited, turbidity did not affect immunogenicity. Immunization with KLH conjugated peptides stimulates Th cells, which in turn contribute to the induction of the B-cell response for antibody generation. Mice were immunized, bled and titers were determined for six representative clones (1E1E, 1E1F, 2D4A, 2D4E, 7E5D and 7E5E), by enzyme-linked immunosorbent assay (ELISA) as shown in Table 1. SEQ ID NO: 2 peptide was used for coating of ELISA plates as antigen (Ag) source to check for the binding activity of six BCMA mAb clones. Clone 1E1E and 2D4A with better binding were used for further analysis.

TABLE 1

BCMA mAb BINDS TO SEQ ID NO: 2 PEPTIDE:

| Cell lines | Supernatant Dilution | | | | | | | |
|---|---|---|---|---|---|---|---|---|
| | 1:10 | 1:30 | 1:90 | 1:270 | 1:810 | 1:2,430 | Blank | Titer | Isotype |
| 1E1E | 3.766 | 3.708 | 3.673 | 3.262 | 2.369 | 0.850 | 0.063 | >1:2,430 | IgG1, k |
| 1E1F | 3.822 | 3.766 | 3.669 | 3.499 | 2.924 | 1.614 | 0.063 | >1:2,430 | IgG1, k |
| 2D4A | 3.839 | 3.792 | 3.659 | 3.244 | 3.001 | 2.242 | 0.063 | >1:2,430 | IgG1, k |
| 2D4F | 3.820 | 3.819 | 3.788 | 3.164 | 2.424 | 1.349 | 0.063 | >1:2,430 | IgG1, k |
| 7E5D | 3.803 | 3.748 | 3.670 | 3.229 | 2.964 | 1.504 | 0.063 | >1:2,430 | IgG1, k |
| 7E5E | 3.781 | 3.742 | 3.633 | 3.195 | 2.889 | 1.343 | 0.063 | >1:2,430 | IgG1, k |

Further, a recombinant expression vector, is selected from the group consisting of a DNA, a RNA, a plasmid, a lentivirus vector or adeno-associated viral vector. In an aspect, the recombinant expression vector comprises EF-1α promoter of SEQ ID NO: 35.

The genetically modified immune effector cells contemplated herein provide improved methods of adoptive immunotherapy for use in the treatment of B cell related conditions that include, but are not limited to immunoregulatory conditions and hematological malignancies.

In particular embodiments, the specificity of a primary immune effector cell is redirected to B cells by genetically modifying the primary immune effector cell with a CAR contemplated herein. In various embodiments, a viral vector is used to genetically modify an immune effector cell with a particular polynucleotide encoding a CAR comprising a anti-BCMA antigen binding domain that binds a BCMA.

Further, FIG. 1 shows schematic representation of the generation single-chain Fragment variable (scFv) from BCMA monoclonal antibody, construction of CAR, expression of CAR on T cells followed by their apoptosis induction of tumor cells. T cells engineered to express CARs are comprised of an extracellular derived scFv by joining the heavy and light chain variable regions of a monoclonal antibody against multiple myeloma specific antigen BCMA. scFv is connected signaling domains via a transmembrane domain. CAR T cells are superior to prior T cell therapies in that a higher-affinity, antibody-like recognition of the multiple myeloma cell is achieved in an HLA-independent fashion. The latter is important since both HLA and TSA processing and presentation are often dysfunctional in tumor cells and involved in immune escape.

BCMA, a differentiating membrane glycoprotein, is overexpressed on the surface of multiple myeloma cells. BCMA expression is associated with worsening tumor progression and chemoresistance, making it an attractive TSA for scFv-mediated immunotherapy.

Figure 2:
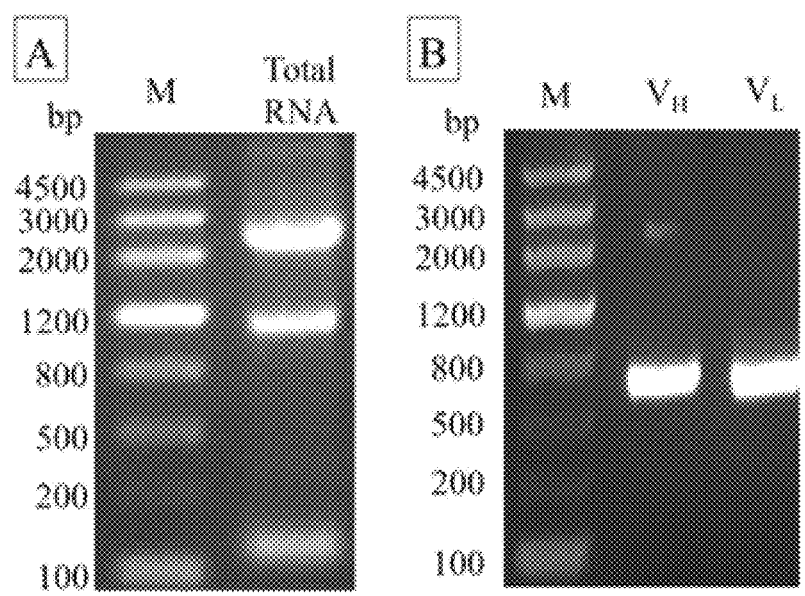
FIG. 2 discloses an embodiment of the invention depicting antigen-binding domain of the BCMA CAR clone 1E1E-amplification of heavy and light chain variable regions.

FIG. 2 shows 1E1E clone amplification of heavy and light chain variable regions. Since mRNA comprises only ~1% of total cellular RNA, it was analyzed that the ribosomal RNA (rRNA) comprises ~80% on agarose gel analysis. In general, 2:1 ratio of 28S and 18S rRNA band intensities observed in gel is indicative of intact RNA. FIG. 1A depicts the quality of total cellular RNA run alongside marker showing 2 bands of 28S and 18S rRNA with ratio ~2:1 reflecting good quality of total RNA preparation. Reverse transcription of total cellular RNA into cDNA was performed using universal primers. RT-PCR was then performed using cDNA template to amplify the variable regions of heavy ($V_H$) and light chains ($V_L$) of the antibody (FIG. 1B). Six single amplified colonies with correct insert sizes were gel purified and sequenced. The consensus sequences were codon optimized for CHO cell expression and $V_H$ and $V_L$ were chemically synthesized.

Figure 3:
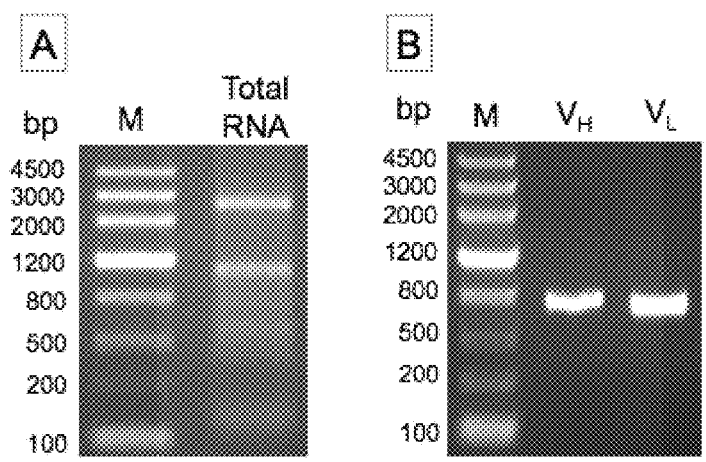
FIG. 3 discloses an embodiment of the invention depicting antigen-binding domain of the BCMA CAR clone 2D4A-amplification of heavy and light chain variable regions.

FIG. 3 shows a 2D4A clone amplification of heavy and light chain variable regions. Since mRNA comprises only ~1% of total cellular RNA, it was analyzed that the ribosomal RNA (rRNA) comprises ~80% on agarose gel analysis. In general, 2:1 ratio of 28S and 18S rRNA band intensities observed in gel is indicative of intact RNA. FIG. 2A depicts the quality of total cellular RNA run alongside marker showing 2 bands of 28S and 18S rRNA with ratio ~2:1 reflecting good quality of total RNA preparation. Reverse transcription of total cellular RNA into cDNA was performed using universal primers.

RT-PCR was then performed using cDNA template to amplify the variable regions of heavy ($V_H$) and light chains ($V_L$) of the antibody (FIG. 2B). Six single amplified colonies with correct insert sizes were gel purified and sequenced. The consensus sequences were codon optimized for CHO cell expression and $V_H$ and $V_L$ were chemically synthesized.

Figure 4:
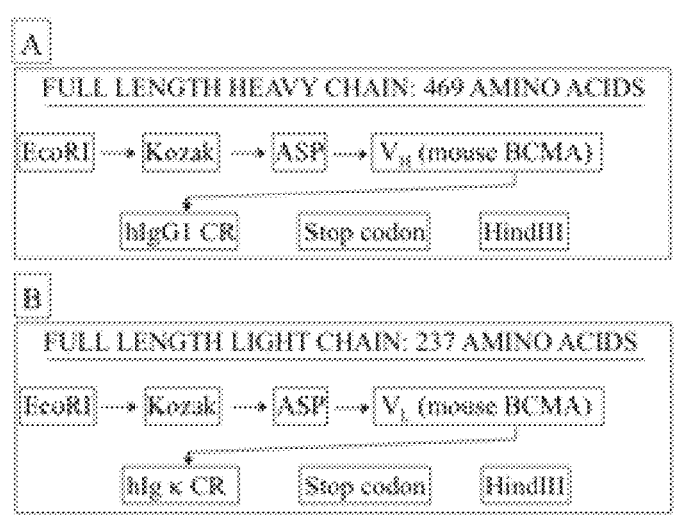
FIG. 4 discloses an embodiment of the invention depicting subcloning to generate full length chimeric BCMA antibody.

FIG. 4 shows cloning strategy or subcloning to generate full length chimeric BCMA antibody i.e. to produce chimeric BCMA mAb. Chimeric BCMA antibody with codon optimized mouse variable region and human constant regions were cloned into pTT5 vectors. Elements of the expression vector include a CMV (Cytomegalovirus) promoter, a mutated origin of replication (pUC-ori), Kozak sequence for translational assistance and leader peptide (signal peptide) to facilitate secretion with flanking 5'EcoRI and 3 'HindIII sites, a polyadenylation signal sequence of rabbit beta-globin and transcription terminator, and elements to allow for the selection. Codon optimized $V_H$ DNA was cloned at the 5' end of human IgG1 heavy chain constant region (FIG. 3A). Similarly, for the light chain constant region, human Ig Kappa (hIg κ) light chain was used (FIG. 3B). Human heavy chain constant region sequence was obtained from database: http://www.uniprot.org/uniprot/P01857. Human light chain constant region sequence was obtained from database: http://www.uniprot.org/uniprot/P01834.

Figure 5:
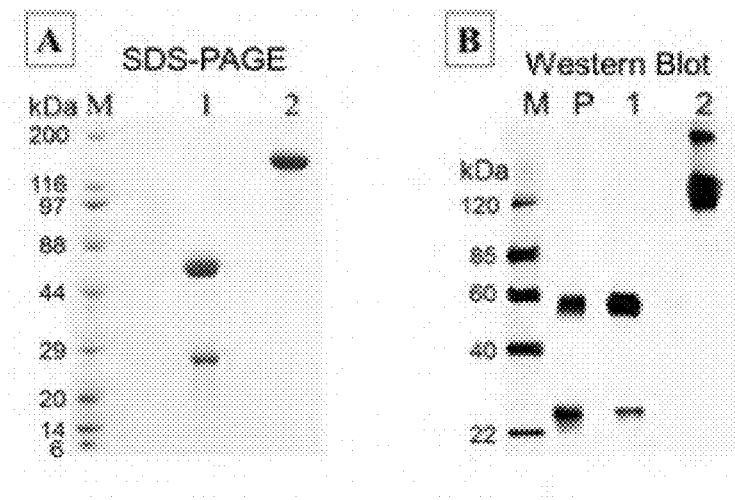
FIG. 5 discloses an embodiment of the invention depicting antigen-binding domain of the BCMA CAR clone 1E1E gene Synthesis, subcloning, transient transfection and purification. Heavy and light chain synthesized DNA sequences of clone 1E1E were subcloned into expression vectors and were transiently co-transfected into CHO-3E7 suspension cultures. Cell cultures were propagated in serum-free FreeStyle™ CHO Expression Medium (Life Technologies, Carlsbad, Calif., USA). On day 6, the cell culture supernatant collected, filtered and antibody was purified by protein A CIP column (GenScript, Cat. No. L00433).

FIG. 5 shows analysis of clone 1E1E of purified chimerized BCMA antibody. The recombinant plasmids encoding chimeric heavy and light chains of BCMA antibody were transiently co-transfected into 200 ml suspension CHO cell cultures. The target antibody was captured from the cell culture supernatant by Protein A affinity chromatography followed by buffer exchange. The heavy and light chains of target antibody were detected with estimated molecular weights of ~55 kDa and ~25 kDa based on SDS-PAGE (FIG. 4A) and Western blot analysis (FIG. 4B) (Concentration: 2 mg/ml; Purity: ~95%).

Figure 6:
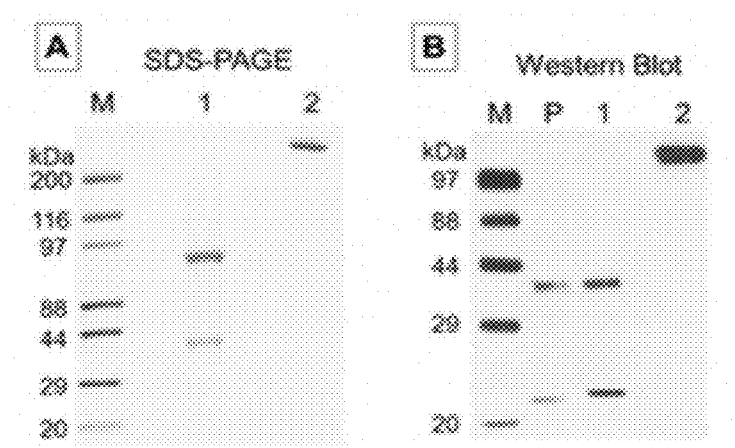
FIG. 6 discloses an embodiment of the invention depicting antigen-binding domain of the BCMA CAR clone 2D4A CHO cell expression and purification of chimeric BCMA antibodies, gene Synthesis, subcloning, transient transfection and purification. Heavy and light chain synthesized DNA sequences of clone 2D4A were subcloned into expression vectors and were transiently co-transfected into CHO-3E7 suspension cultures. Cell cultures were propagated in serum-free FreeStyle™ CHO Expression Medium (Life Technologies, Carlsbad, Calif., USA). On day 6, the cell culture supernatant collected, filtered and antibody was purified by protein A CIP column (GenScript, Cat. No.
Figure 7A:
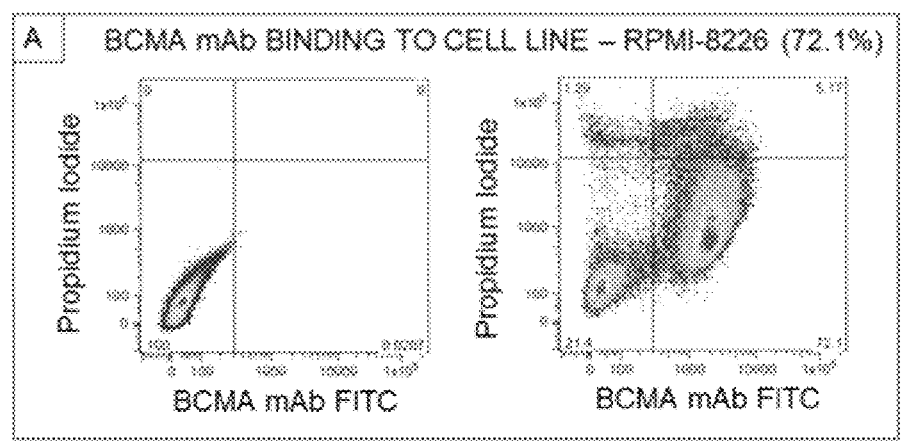
FIG. 7A discloses an embodiment of the invention depicting flow cytometric analysis for the cell surface expression of BCMA on multiple myeloma (MM) cell line RPMI-8226.
Figure 7B:
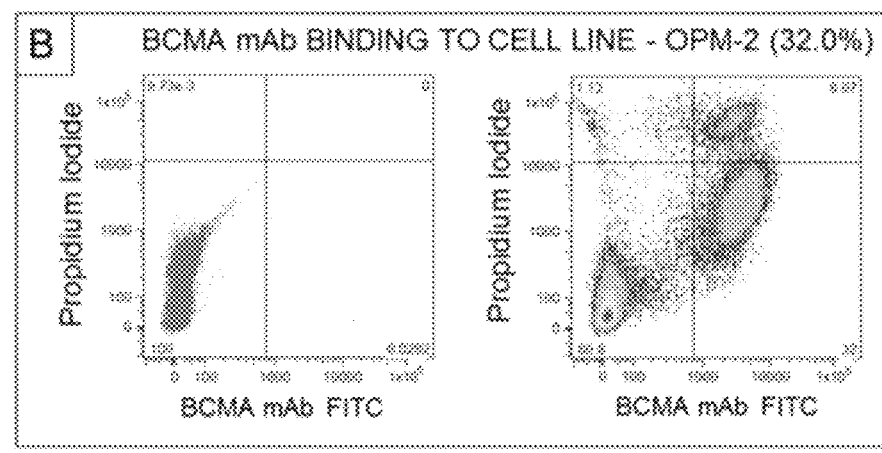
FIG. 7B discloses an embodiment of the invention depicting flow cytometric analysis for the cell surface expression of BCMA on multiple myeloma (MM) cell line OPM-2.
Figure 7C:
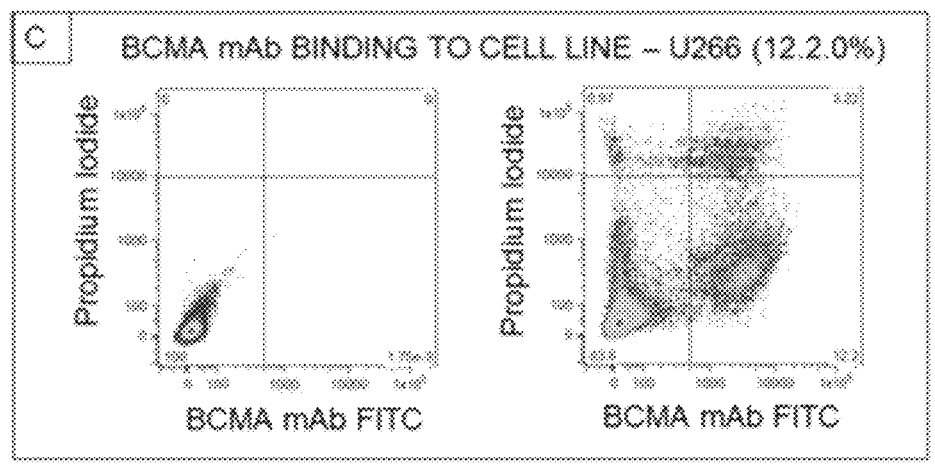
FIG. 7C discloses an embodiment of the invention depicting flow cytometric analysis for the cell surface expression of BCMA on multiple myeloma (MM) cell line U266.
Figure 7D:
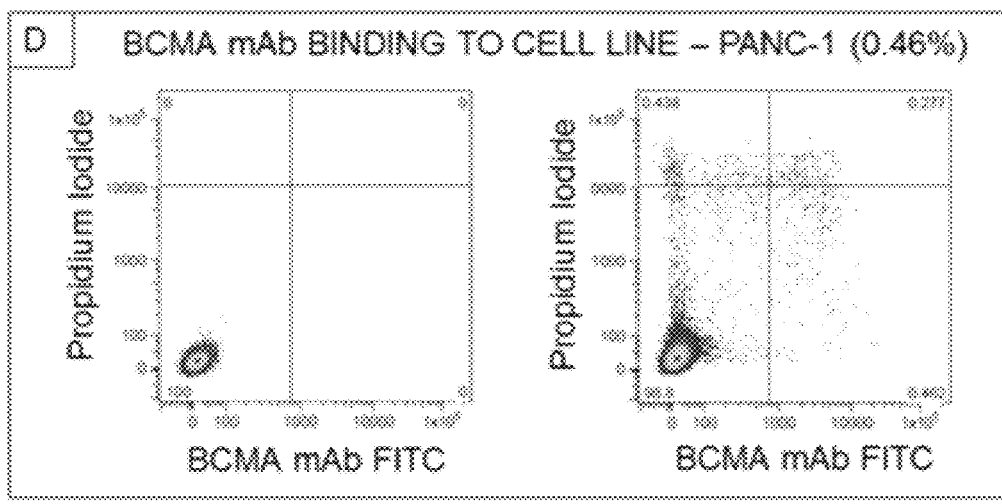
FIG. 7D discloses an embodiment of the invention depicting flow cytometric analysis for the cell surface expression of BCMA on pancreatic cancer cell line PANC-1.
Figure 7E:
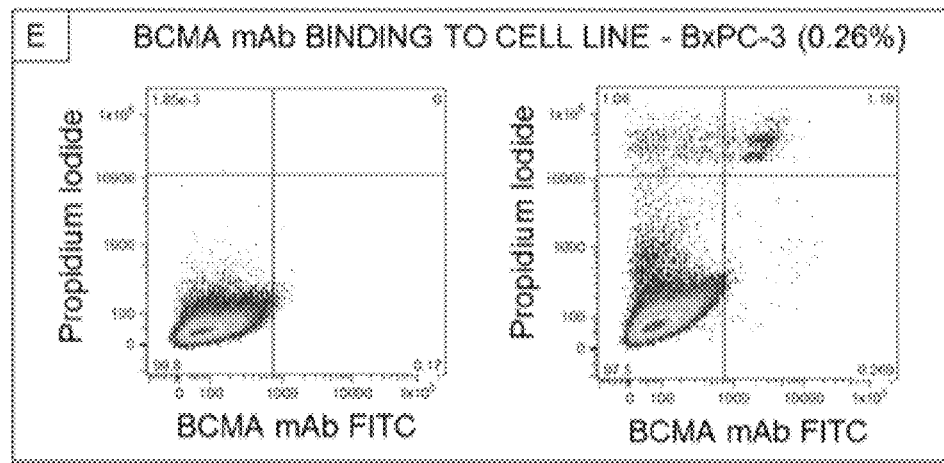
FIG. 7E discloses an embodiment of the invention depicting flow cytometric analysis for the cell surface expression of BCMA on pancreatic cancer cell line BxPC-3.
Figure 7F:
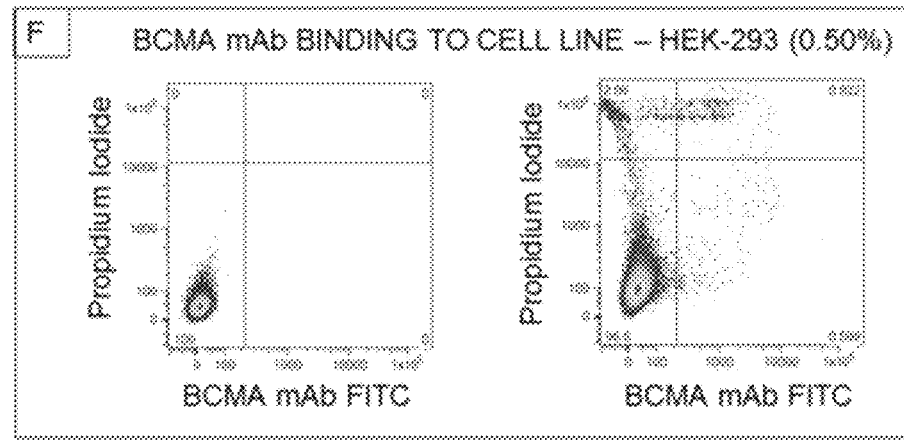
FIG. 7F discloses an embodiment of the invention depicting flow cytometric analysis for the cell surface expression of BCMA on human embryonic kidney cell line HEK-293.
Figure 7G:
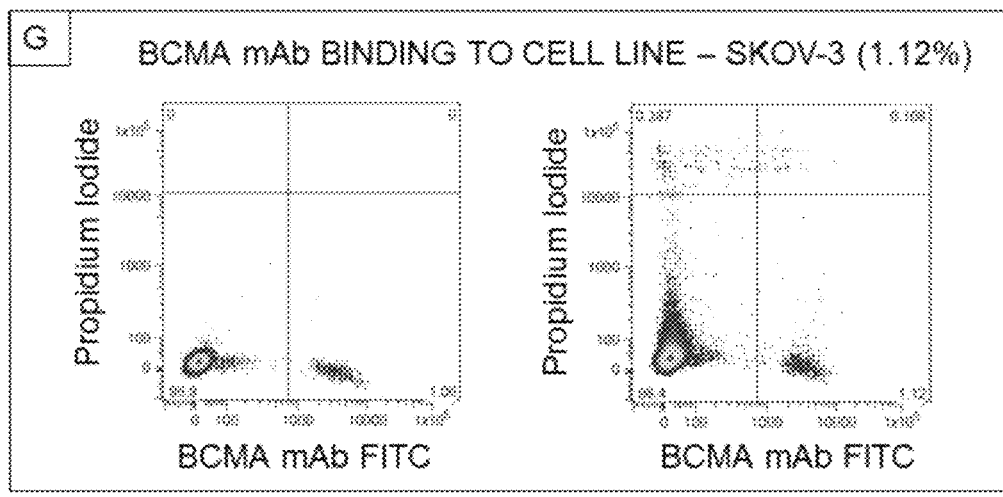
FIG. 7G discloses an embodiment of the invention depicting flow cytometric analysis for the cell surface expression of BCMA on ovarian cancer cell line SKOV-3.

FIG. 6 shows analysis of a clone 2D4A CHO cell expression and purification of chimeric BCMA antibodies. The recombinant plasmids encoding chimeric heavy and light chains of BCMA antibody were transiently co-transfected into 200 ml suspension CHO cell cultures. The target antibody was captured from the cell culture supernatant by Protein A affinity chromatography followed by buffer exchange. The heavy and light chains of target antibody were detected with estimated molecular weights of ~55 kDa and ~25 kDa based on SDS-PAGE (FIG. 5A) and Western blot analysis (FIG. 5B) (Concentration: 2 mg/ml; Purity: ~95%).

FIG. 7 shows analysis of clone 1E1E the binding of ANTI-BCMA mAb to multiple myeloma (MM) cell lines. Purified chimeric BCMA antibodies were evaluated with a flow cytometry-binding assay using various cell lines. The binding of purified anti-chimeric BCMA antibodies to three multiple myeloma cell lines, with RPMI 8226 showing 72% FIG. 7A), OPM-2 showing 32% (FIG. 7B), and U266 showing 12.2% (FIG. 7C), of cells binding to chimeric mAb was tested. Further, binding analysis with PANC-1 cell line showing 0.46% (FIG. 7D), BxPC-3 showing 0.26% (FIG. 7E), HEK-293 showing 0.50% (FIG. 7F), and SKOV-3 cell line showing 1.12% binding (FIG. 7G) was carried out. Propidium iodide (PI) staining indicated that more than 90% cells are alive in all the experiments. The flow cytometric analysis of binding activity clearly indicated the binding of BCMA chimeric mAb to multiple myeloma cell lines (RPMI-8226, OPM-2 and U266) but not with pancreatic cancer (PANC-1 and BxPC-3), human embryonic kidney cells (HEK-293) and ovarian cancer (SKOV-3).

Figure 8:
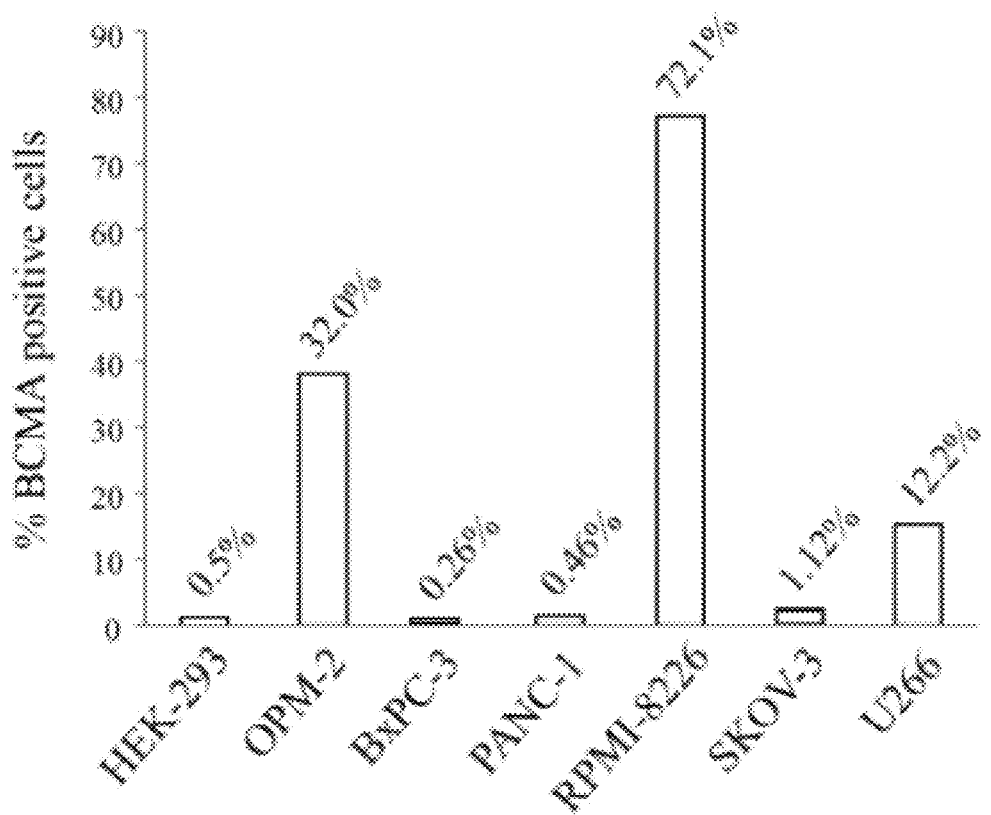
FIG. 8 discloses an embodiment of the invention depicting bar diagram for analysis of the binding of anti-BCMA mAb to various cancer cell lines.

FIG. 8 shows analysis of the binding of ANTI-BCMA mAb to various cancer cell lines. The flow cytometric assay results were depicted in the bar diagram for the % binding of BCMA chimeric mAb to various cell lines from multiple myeloma (RPMI-8226, OPM-2 and U266), epithelial ovarian cancer (SKOV-3), human embryonic kidney (HEK-293) and pancreatic cancer (PANC-1 and BxPC-3).

Figure 9:
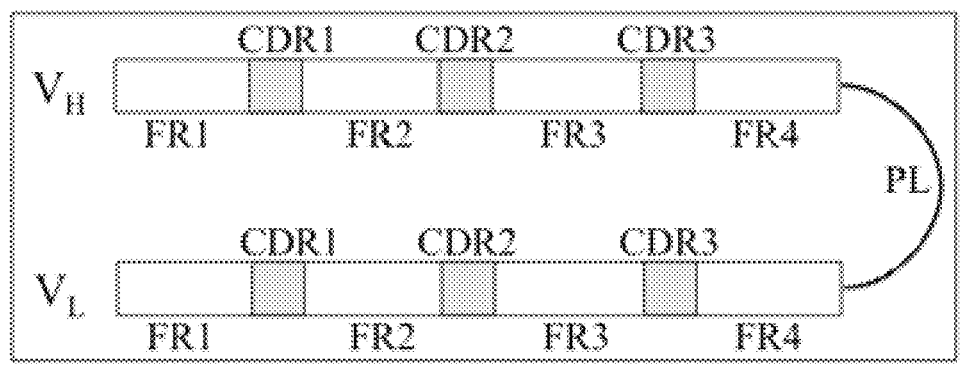
FIG. 9 discloses an embodiment of the invention depicting schematic representation of single-chain fragment variable (scFv) with 6 complementary determining regions.

FIG. 9 shows schemetic representation of single-chain fragment variable (scFv) with 6 complementary determining regions. Schematic representation of the antibody fragments encoding variable regions of heavy ($V_H$) and light chains ($V_L$) of BCMA for the construction of CAR expression plasmid as well as in lentiviral expression system is shown. Variable domains of both $V_H$ and $V_L$ sequences are composed of 3 complementarity-determining regions each (CDR1, CDR2 and CDR3) where antigen binds and 4 framework regions (FR1, FR2, FR3 and FR4). Smallest fragment of mAb that determines antigen binding is generally a pair of $V_H$ and $V_L$ domains which when connected by a flexible peptide linker are known as single-chain fragment variable (scFv), which contains all 6 CDRs ($V_H$+$V_L$).

Figure 10:
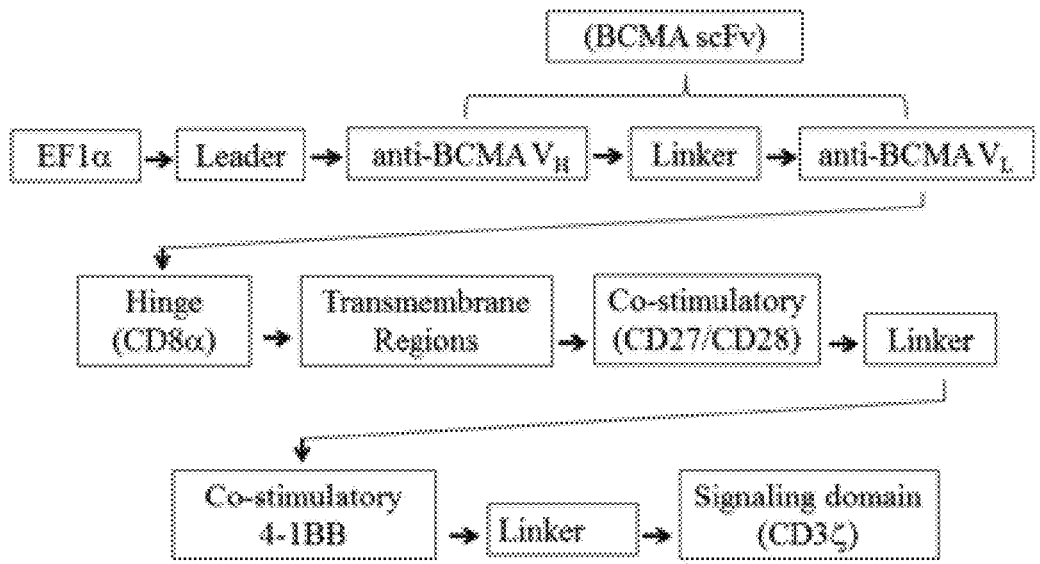
FIG. 10 discloses an embodiment of the invention depicting schematic diagram of construction of codon optimized chimeric antigen receptor (CAR) with BCMA scFv.

FIG. 10 shows construction of codon optimized chimeric antigen receptor (CAR) with BCMA scFv. The sequence of CAR with the following pattern is designed: Towards extracellular end, the BCMA scFv is connected to hinge CD28 spanning transmembrane region. The cytoplasmic portion of the CD27/CD28 is connected to another co-stimulator molecule 4-1BB which is further linked to the cytoplasmic portion of the CD3ζ molecule. DNA encoding the CARs was codon optimized and the vector construction work was out-sourced to Cyagen Biosciences (Santa Clara, USA). Correct assembly of the third generation BCMA CAR construct was validated by DNA sequence analyses.

Figure 11A:
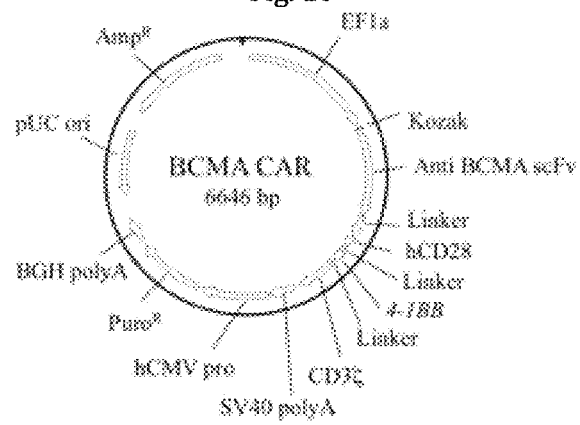
FIG. 11A discloses an embodiment of the invention depicting plasmid expression vector for BCMA Chimeric Antigen Receptor (CAR).
Figure 11B:
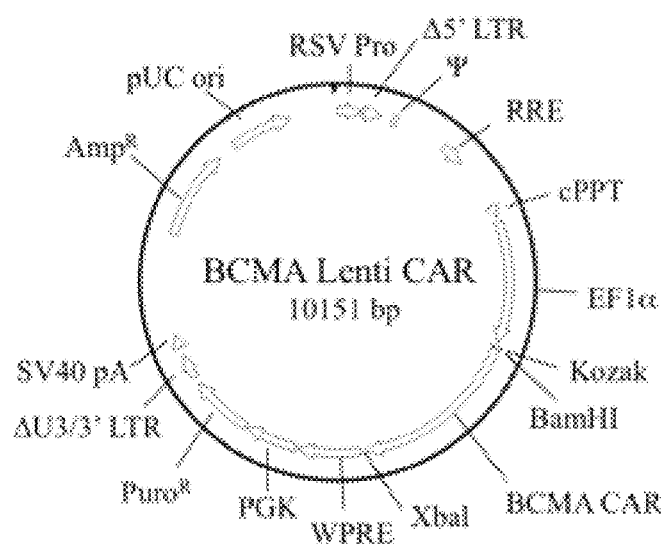
FIG. 11B discloses an embodiment of the invention depicting Lentiviral expression vector for BCMA Chimeric Antigen Receptor (CAR).

FIG. 11 shows construction of BCMA chimeric antigen receptor (CAR) expression plasmid and lentiviral vector. The BCMA CAR expression cassette in both plasmid and lentiviral format are driven by EF1α promoter suitable for expression in NK and T cells. The CAR construct has EGFP and puromycin co-expression. BCMA binding single chain fragment variable (scFv) sequences were derived codon optimized 1E1E for the expression in human cells. The third-generation CAR expression cassette comprises cell surface scFv linked to CD8α hinge and transmembrane region with intracellular CD27 or CD28, 4-1BB and CD3ζ chain. The CAR-encoding cassette was sub-cloned into either an expression plasmid vector (FIG. 11A) or lentiviral expression vector (FIG. 11B).

Figure 12:
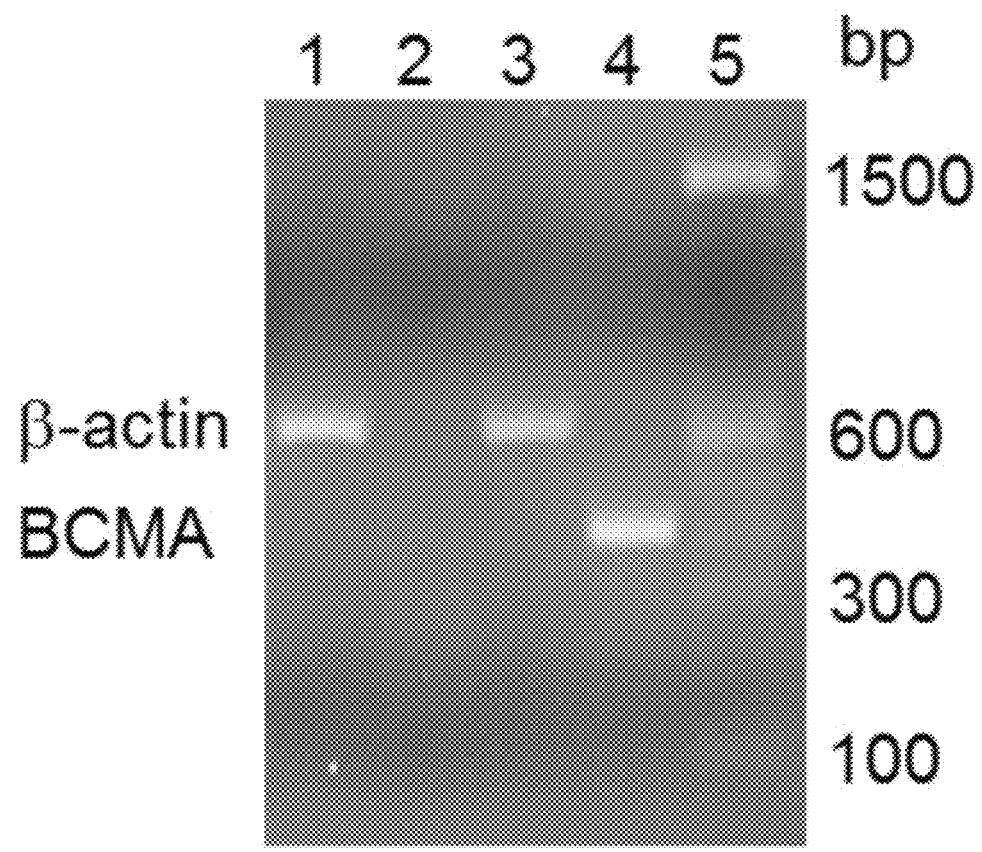
FIG. 12 discloses an embodiment of the invention depicting BCMA-CAR vector transduced cells express BCMA in NK-92 cells.

FIG. 12 shows BCMA-CAR vector transduced cells express BCMA in NK-92 cells. To identify the expression of BCMA in the CAR vector transduced cells, total RNA was isolated followed RT-PCR analysis of both β actin and BCMA. While observed the amplification of β-actin in both control and vector transduced cells (FIG. 12, lanes 1 and 3 respectively), only CAR vector transduced cells showed the expression of BCMA (FIG. 12, lane 4).

Figure 13:
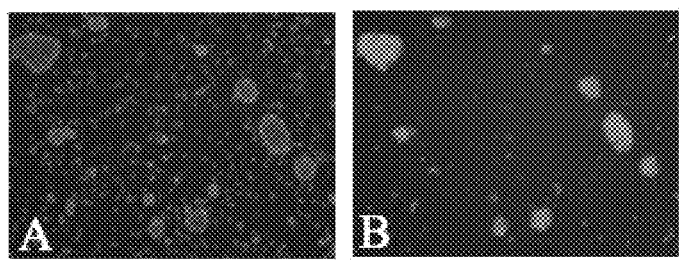
FIG. 13 discloses an embodiment of the invention showing lentiviral transduction efficiency >70% as determined by phase contrast microscopy and by EGFP expression.

FIG. 13 shows lentiviral transduction efficiency >70% as determined by EGFP expression. Shown are representative images of phase contrast microscopy (FIG. 13A) along with fluorescent expression (FIG. 13B).

Figure 14:
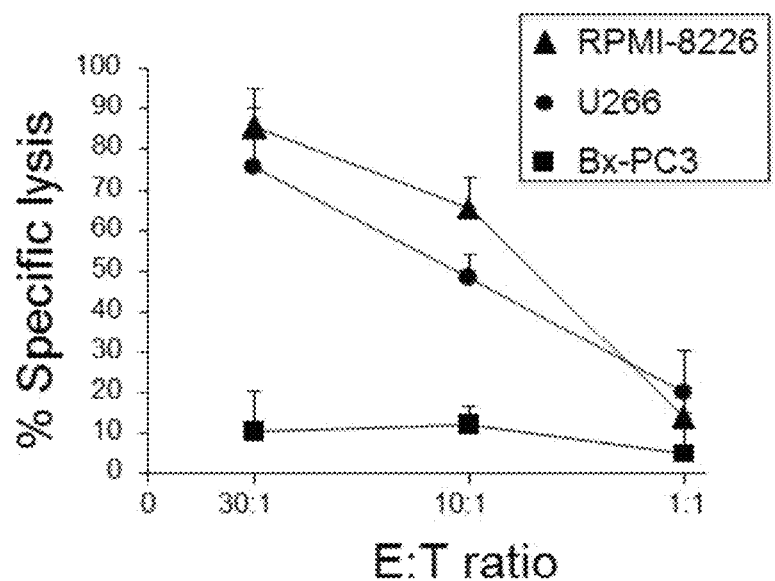
FIG. 14 discloses an embodiment of the invention depicting cytotoxicity of BCMA-CAR-NK-92 cells.

FIG. 14 shows cytotoxicity of BCMA-CAR-NK-92 cells. To determine whether the BCMA-CAR expressing NK-92 cells could induce cell death against BCMA-expressing targets, two human multiple myeloma cell lines positive for BCMA (RPMI-8226 and U266) expression and one human pancreatic cancer cell line negative for BCMA (Bx-PC3) were tested. Over 75% lysis of target cells is observed for both the multiple myeloma cell lines at E:T ratio of 30:1. Even when E:T ratio was as low as 10:1, the cytotoxicity was more than 55%. The above effects were not observed in targeting Bx-PC3 human pancreatic cancer cells that are negative for BCMA expression.

Figure 15:
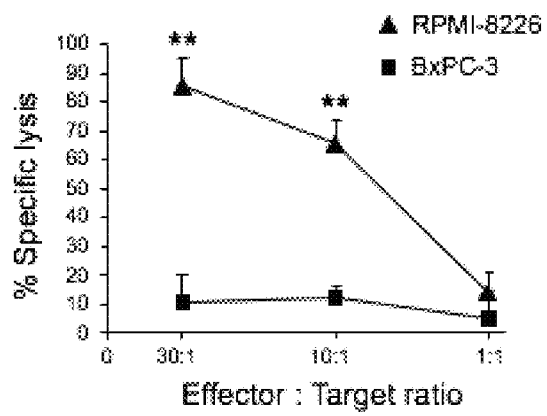
FIG. 15 discloses an embodiment of the invention depicting cytotoxicity of human multiple myeloma cell line RPMI-8226 (Target) by BCMA-CAR T-cells (Effector).

FIG. 15 shows cytotoxicity of BCMA-CAR-NK-92 cells on RPMI-8226. To determine whether the BCMA-CAR expression on NK-92 cells could induce cell death against BCMA-expressing human multiple myeloma cell line RPMI-8226 using BxPC-3 human pancreatic cancer cell line as negative were tested. Over 75% lysis of target cells is observed for both the multiple myeloma cell lines at E:T ratio of 30:1. Even when E:T ratio was as low as 10:1, the cytotoxicity was more than 55%. The above effects were not observed in targeting Bx-PC3 human pancreatic cancer cells that are negative for BCMA expression. Data is representative of at least 3 separate experiments. **$P<0.01$.

Figure 16:
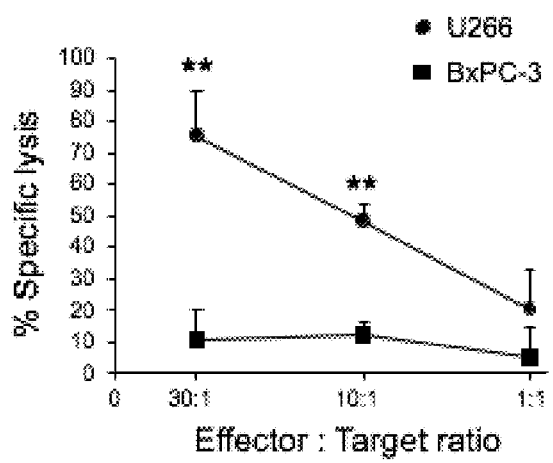
FIG. 16 discloses an embodiment of the invention depicting cytotoxicity of human multiple myeloma cell line U266 (Target) by BCMA-CAR T-cells (Effector).

FIG. 16 shows cytotoxicity of BCMA-CAR-NK-92 cells on U266. To determine whether the BCMA-CAR expression on NK-92 cells could induce cell death against BCMA-expressing target U266, human multiple myeloma cell line and Bx-PC3, human pancreatic cancer cell line negative for BCMA were tested. Over 75% lysis of target cells is observed for both the multiple myeloma cell lines at E:T ratio of 30:1. Even when E:T ratio was as low as 10:1, the cytotoxicity was more than 55%. The above effects were not observed in targeting Bx-PC3 human pancreatic cancer cells that are negative for BCMA expression. Data is representative of at least 3 separate experiments. **P<0.01.

Figure 17A:
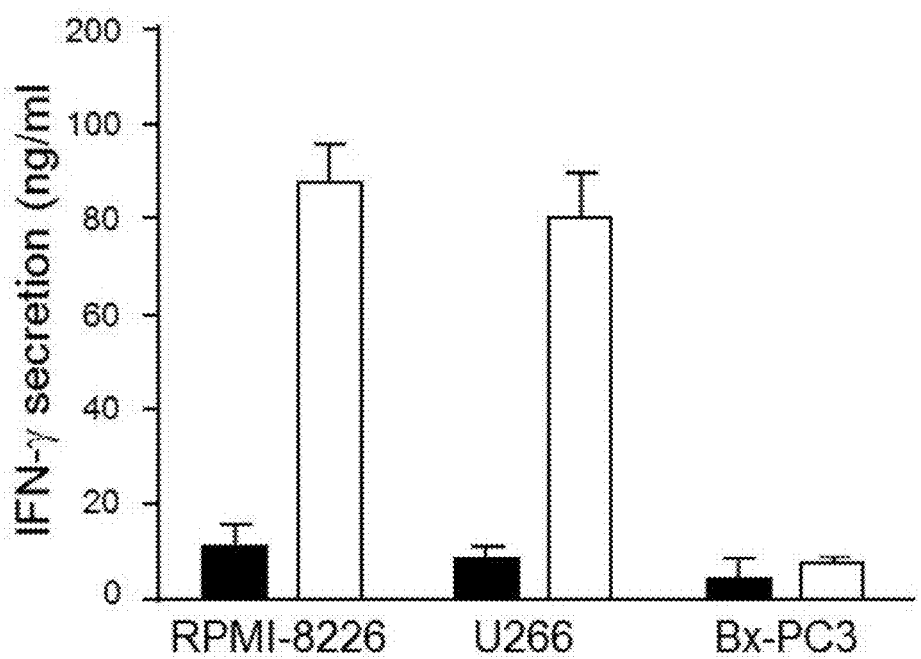
FIG. 17A discloses an embodiment of the invention depicting secretion of interferon-γ.
Figure 17B:
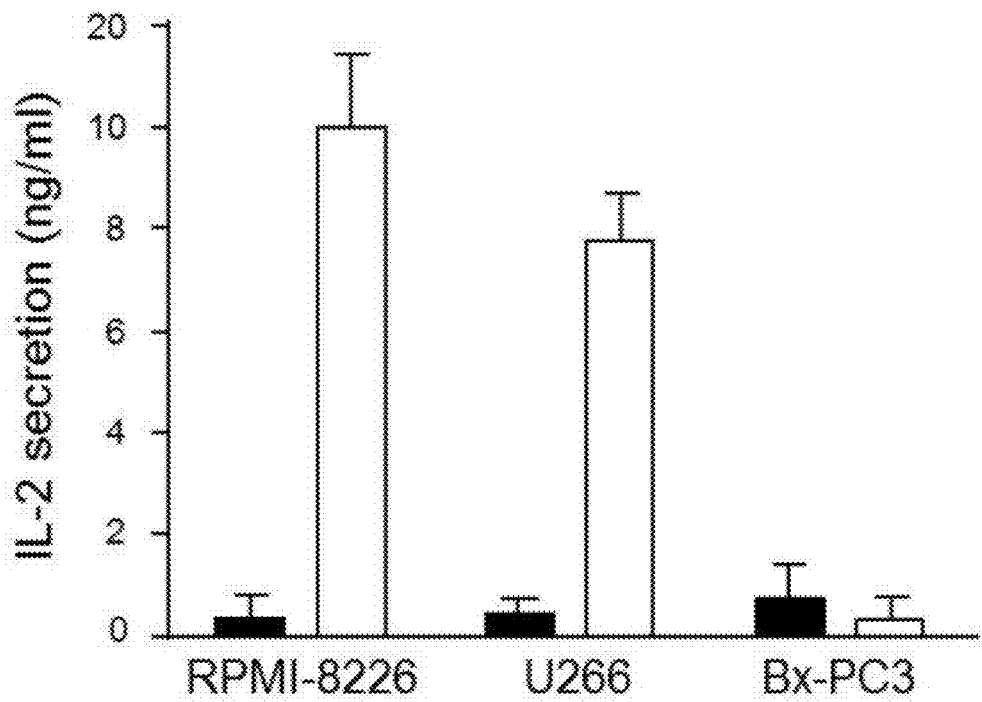
FIG. 17B discloses an embodiment of the invention depicting secretion of IL-2.

FIG. 17 shows secretion of high levels of interferon-γ AND IL-2. Recognition of multiple myeloma cells by BCMA-CAR-NK-92 cells should result in the activation through signal transduction by CD27/28 co-stimulatory molecule which is part of CAR construct. This process of activation of NK-92 cells not only enhance cytotoxicity, but also induce IFN-γ and IL-2 secretion leading to enhanced immune surveillance and activation of cytotoxic CD8$^+$ T cells and macrophages resulting in further cytolysis multiple myeloma cells. To determine this activation, IFN-γ, and IL-2 secretions were measured in the cell-free supernatants of co-cultures of BCMA-CAR-NK-92 and two human multiple myeloma cell lines positive for BCMA (RPMI-8226 and U266) expression and one human pancreatic cancer cell line negative for BCMA (Bx-PC3) were tested. Mock-transduced NK-92 cells produced negligible levels of IFN-γ and IL-2 in both positive and negative cell lines for BCMA expression. Co-cultures of BCMA-CAR transduced NK-92 multiple myeloma cell lines (RPMI-8226 and U266) showed significantly greater levels of IFN-γ (FIG. 17A) and IL-2 (FIG. 17B) with no significant change in the Bx-PC3 cell lines indicating BCMA-CAR-NK-92 cell activation only when they encounter cell-surface BCMA.

Figure 18:
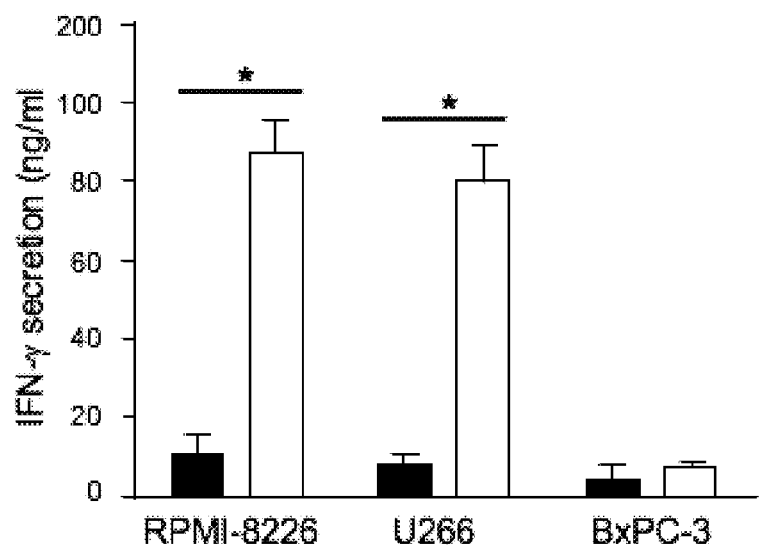
FIG. 18 discloses an embodiment of the invention depicting secretion of IFN-γ in the co-cultures of BCMA-CAR T-cells with, (1) human multiple myeloma cell lines RPMI-8226, (2) U266 and (3) human pancreatic cancer cell line BxPC-3.

FIG. 18 shows secretion of high levels of interferon-γ. Recognition of multiple myeloma cells by BCMA-CAR-NK-92 cells should result in the activation through signal transduction by CD28 co-stimulatory molecule which is part of CAR construct. This process of activation of NK-92 cells not only enhance cytotoxicity, but also induce IFN-γ secretion leading to enhanced immune surveillance and activation of cytotoxic CD8$^+$ T cells and macrophages resulting in further cytolysis multiple myeloma cells. To determine this activation, IFN-γ secretions was measured in the cell-free supernatants of co-cultures of BCMA-CAR-NK-92 and two human multiple myeloma cell lines positive for BCMA (RPMI-8226 and U266) expression and one human pancreatic cancer cell line negative for BCMA (Bx-PC3) were tested. Mock-transduced NK-92 cells produced negligible levels of IFN-γ. Co-cultures of BCMA-CAR transduced NK-92 multiple myeloma cell lines (RPMI-8226 and U266) showed significantly greater levels of IFN-γ with no significant change in the Bx-PC3 cell lines indicating BCMA-CAR-NK-92 cell activation only when they encounter cell-surface BCMA. Data is representative of at least 3 separate experiments. *P<0.05.

Figure 19:
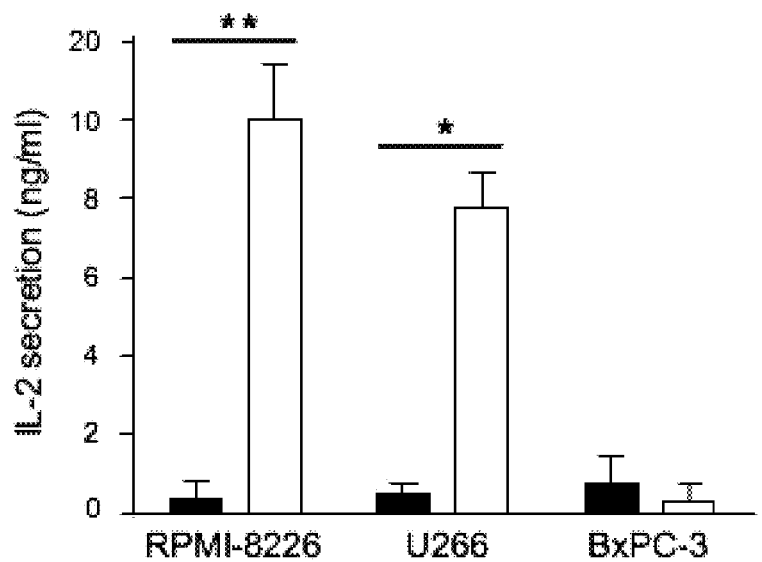
FIG. 19 discloses an embodiment of the invention depicting secretion of IL-2 in the co-cultures of BCMA-CAR T-cells with, (1) human multiple myeloma cell lines RPMI-8226, (2) U266 and (3) human pancreatic cancer cell line BxPC-3.

FIG. 19 shows secretion of high levels of IL-2. Recognition of multiple myeloma cells by BCMA-CAR-NK-92 cells should result in the activation through signal transduction by CD28 co-stimulatory molecule which is part of CAR construct. This process of activation of NK-92 cells not only enhance cytotoxicity, but also induce IL-2 secretion leading to enhanced immune surveillance and activation of cytotoxic CD8$^+$ T cells and macrophages resulting in further cytolysis multiple myeloma cells. To determine this activation, IL-2 secretions was measured in the cell-free supernatants of co-cultures of BCMA-CAR-NK-92 and two human multiple myeloma cell lines positive for BCMA (RPMI-8226 and U266) expression and one human pancreatic cancer cell line negative for BCMA (Bx-PC3) were tested. Mock-transduced NK-92 cells produced negligible levels of IL-2. Co-cultures of BCMA-CAR transduced NK-92 multiple myeloma cell lines (RPMI-8226 and U266) showed significantly greater levels of IL-2 with no significant change in the Bx-PC3 cell lines indicating BCMA-CAR-NK-92 cell activation only when they encounter cell-surface BCMA. Data is representative of at least 3 separate experiments. *P<0.05, **P<0.01.

Figure 20:
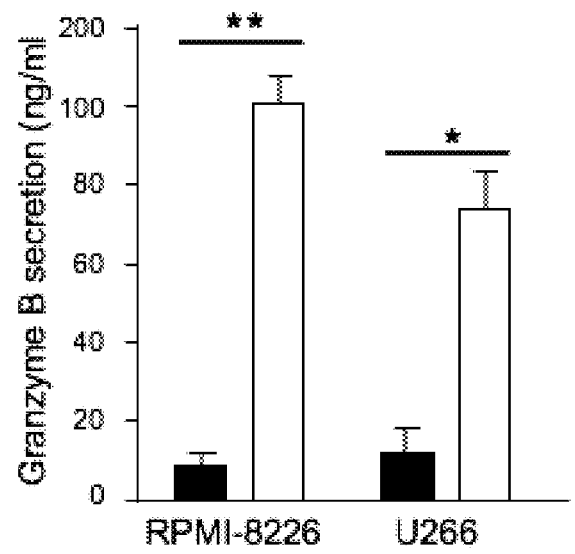
FIG. 20 discloses an embodiment of the invention depicting secretion of Granzyme B in the co-cultures of BCMA-CAR T-cells with, (1) human multiple myeloma cell lines RPMI-8226 and (2) U266.

FIG. 20 shows secretion of high levels of Granzyme B. Recognition of multiple myeloma cells by BCMA-CAR-NK-92 cells should result in the activation through signal transduction by CD28 co-stimulatory molecule which is part of CAR construct. This process of activation of NK-92 cells not only enhance cytotoxicity, but also induce Granzyme B secretion leading to enhanced immune surveillance and activation of cytotoxic CD8$^+$ T cells and macrophages resulting in further cytolysis multiple myeloma cells. To determine this activation, Granzyme B secretions was measured in the cell-free supernatants of co-cultures of BCMA-CAR-NK-92 and two human multiple myeloma cell lines positive for BCMA (RPMI-8226 and U266) expression and one human pancreatic cancer cell line negative for BCMA (Bx-PC3) were tested. Mock-transduced NK-92 cells produced negligible levels of Granzyme B. Co-cultures of BCMA-CAR transduced NK-92 multiple myeloma cell lines (RPMI-8226 and U266) showed significantly greater levels of Granzyme B with no significant change in the Bx-PC3 cell lines indicating BCMA-CAR-NK-92 cell activation only when they encounter cell-surface BCMA. Data is representative of at least 3 separate experiments. *P<0.05, **P <0.01.

According to an embodiment of the invention, a method for generation of chimeric antigen receptors (CARs) which are specific to B-cell maturation antigen (BCMA) includes transducing cells with said B-cell maturation antigen (BCMA) specific a chimeric antigen receptor (CAR) vector to generate genetically engineered cells. The genetically engineered cells are selected from the group consisting of human T lymphocytes, natural killer cells (NK cells), NK-92 cells, and natural killer T cells (NKT cells).

These cells are administered to subject with multiple myeloma, other hematological malignancies and any precancerous conditions, wherein at least a subpopulation of the cells of said cancer expresses BCMA. The cells expressing a CAR are administered in combination with chemotherapeutic agent that ameliorates side effects and increase therapeutic benefit.

In particular embodiments, methods comprising administering a therapeutically effective amount of CAR-expressing immune effector cells contemplated herein or a composition comprising the same, to a patient in need thereof, alone or in combination with one or more therapeutic agents.

Reference is now made to the following example, which together with the above descriptions including method illustrates some embodiment of the invention without limiting the scope of the invention.

Example 1

Generally, the nomenclature used herein and the laboratory procedures utilized in the present invention include molecular, biochemical, microbiological and recombinant DNA techniques.
Step 1: Immunization with BCMA Peptide KLH Conjugte:
Surface exposed peptide epitope of BCMA (SEQ ID NO: 1) (Sequence of Antigen) was selected using software program OptimumAntigen™ (Genscript, USA). Selected peptide was further added with Cysteine and Proline amino acid residues at N terminal end (SEQUENCE ID NO: 2) (Modified sequence of Antigen) to increase the immunogenicity. Though addition of these amino acids increases immunogenicity, peptides in general by themselves are too small to elicit a sufficient immune response and conjugated SEQ ID NO: 2 to keyhole limpet hemocyanin (KLH), which is known to be an ideal carrier for use in mice and has a higher immunogenicity than does BSA. Mice were immunized with SEQ ID NO: 2-KLH conjugate followed by 2 booster doses. Hybridoma was generated with fusion of isolated splenocytes and myeloma cell line. Six specific clones were selected and grown for further evaluation.

Step 2: Enzyme Linked Immunosorbant Assay (ELISA):

Hybridoma supernatants from six different clones were screened for their binding to SEQ ID NO: 2 by ELISA. Briefly, ELISA plates were quoted with 100 µl/well of SEQ ID NO: 2 peptide (1 µg/ml). Anti-mouse IgG-horseradish peroxidase conjugate was used as secondary antibody. Serial dilutions of mAb (1:10 through 1:2,500) were used to determine titers. Samples were tested in triplicates to determine mean titers.

Step 3: Total RNA Extraction & cDNA Synthesis:

Total cellular RNA was isolated from the hybridoma following the technical manual of TRIzol Plus RNA Purification System (Invitrogen, Grand Island, N.Y., USA). The isolated total RNA was run alongside a DNA marker Marker III (TIANGEN, Palo Alto, Calif., USA) on a 1.5% agarose gel followed by GelRed staining (Genscript, Piscataway, N.J., USA). Reverse transcription of total cellular RNA into cDNA was carried out with universal primers following the technical manual of SuperScript™ III First-Strand Synthesis System (Invitrogen, Grand Island, N.Y., USA). The antibody fragments encoding variable regions of heavy ($V_H$) and light chains ($V_L$) of BCMA were PCR amplified along with signal sequences. Colony PCR screening was performed to identify clones with inserts of correct sizes. Six single colonies with inserts of correct sizes were sequenced for each antibody fragment.

Step 4: Cloning of Antibody Genes for Transient Expression in Cho Cells:

The $V_H$ and $V_L$ chains were cloned into individual pTT5 for CHO cell expression (Genscript, USA). CHO cells were grown in serum free FreeStyle™ CHO Expression Medium (Life Technologies, Carlsbad, Calif., USA). The cells were maintained in Erlenmeyer Flasks (Corning Inc., Acton, Mass.) at 37° C. with 5% $CO_2$ on an orbital shaker. The recombinant plasmids encoding heavy and light chains of Chimeric BCMA mAb were transiently co-transfected into CHO cells using transfection reagent polyethylenimine. Cell-free supernatant from 1 L of transfected cultures were collected on day 6 for purification of the antibody.

Step 5: Purification and Analysis:

Cell culture broth was centrifuged, followed by filtration. Filtered supernatant was loaded onto Protein A CIP column 5 ml (GenScript, Piscataway, N.J., USA) at 1.0 ml/min. After washing and elution with appropriate buffer, the eluted fractions were pooled and either buffer exchanged to PBS, pH 7.2 or neutralized with 1M Tris-HCl, pH 9.0. The purified protein was analyzed by SDS-PAGE and Western blot by using standard protocols for molecular weight, yield and purity measurements. The secondary antibody for Western blot was anti Human IgG conjugated with horseradish peroxidase (H&L, GOAT, Rockland, Limerick, Pa., USA).

Step 6: Construction of Chimeric Antigen Receptor (CAR) Vectors:

The BCMA-scFv fragment, amplified from the hybridoma cell line 1E1E was used in the construction of CAR vector. The variable heavy ($V_H$) and light ($V_L$) chains were connected by a peptide linker and incorporated in frame with the CD28-CD3ζ domains. The entire CAR plasmid vectors were constructed using the services of VectorBuilder (Cyagen Biosciences Inc. CA). The exact sequences of various components of CAR were obtained from Genbank. Plasmid DNA encoding the full-length CAR construct was also ligated into lentiviral backbone to for the generation of lentiviral vectors.

Step 7: Electroporation and/or Lentiviral Transduction of NK-92 Cells:

NK-92 cells were cultivated in MyeloCult™ H5100 medium (STEMCELL, Cambridge, Mass.) supplement with antibiotics. Cells are sensitive to overgrowth so the cells are split and medium is replaced medium every $2^{nd}$ day maintaining cell density at $3\times10^5$ cells/ml. Amaxa® Cell Line Nucleofector® Kit R is used for electroporation of NK-92 cells (Lonza, Walkersville, Md.). Lentiviral VSVG pseudotyped vector generation was outsourced to VectorBuilder (Cyagen Biosciences Inc. CA). Viral transductions were performed for three consecutive days in 6 well plates using $2\times10^6$ cells in a total volume of 2 mL of lentiviral supernatant containing 8 µg/mL polybrene (Sigma-Aldrich, St. Louis, Mo., USA) and 1000 IU/mL human IL-2. Cells were centrifuged at 1,800 rpm at 32° C. for 45 min, then plates were placed in an incubator at 37° C. for 2 hours.

Step 8: Interferon-γ (IFN-γ), IL-2 and Granzyme B Assays:

A total of $2\times10^5$ target (T) cells of RPMI-8226, U266 multiple myeloma and Bx-PC3 pancreatic cancer cells were co-cultured with various concentrations of NK-92 effector (E) cells in 96 well plates for 48 h. Cell-free supernatants were stored in a negative 80° C. freezer until the assays. IFN-γ, IL-2 and granzyme B secretion was measured by ELISA kit (R&D Systems, Minneapolis, Minn.) according to the manufacturer's instructions. Data represent mean values of triplicates.

Step 9: Reverse Transcription Polymerase Chain Reaction (RT-PCR):

Total RNA was isolated from BCMA-CAR-NK-92 cells using the TRIzol reagent. RT-PCR was performed with the SuperScript III One-Step RT-PCR System (Invitrogen, Carlsbad, Calif.) using BCMA Forward primer (5' GAGTGGCTGGCACACATCTA 3') and BCMA reverse primer (5' AGGAGAAGGACCCCACAAGT 3') with amplicon size of 398 base pairs.

Step 10: Cytotoxicity Assays:

A total of $5\times10^6$ NK-92 cells were electroporated with BCMA-CAR using Amaxa Nucleofector Kit R (Lonza, Walkersville, Md.). Following electroporation, the cells were propagated in recovery medium with 1000 IU/ml recombinant human IL-2 for 24 h prior to further manipulations. Cytotoxicity assays were performed using a non-radioactive lactate dehydrogenase (LDH) detection kit.

Step 11: Flow Cytometric Analysis of Cell Lines for BCMA Expression:

Cell lines were pretreated with normal mouse serum to block nonspecific binding sites in cell staining buffer (BioLengend, USA). Cells were incubated with purified chimeric anti-BCMA mAb (Clone 1E1E) for 30 minutes on ice at 1 µg/ml, followed by washing. Cells were further incubated with secondary antibody conjugated to fluorescein isothiocyanate (FITC) followed by washing and addition of Propidium iodide (PI) before analysis by flow cytometer.

Step 12: Fluorescence Microcopy:

Enhanced green fluorescent protein (EGFP) expression was visualized under the Zeiss Observer.A1 fluorescence microscope and the images were captured using the cooled Axio CAM CCD camera. The same microscopic fields were viewed and photographed by phase contrast microscopy.

Step 13: Statistical Analysis

Data are expressed as mean±standard deviation from at least three independent experiments. Student's t-test was employed to evaluate differences between groups. All P values are 2-sided, with ≤0.05 being statistically significant.

The present invention is however not limited to the above embodiments disclosed above and referred in FIGS. 1 to 13 and other embodiments within the scope of the invention can be used for achieving the result of the present invention without limiting the scope of the invention.

REFERENCES

1. Dotti, G.; RAMOS, C. A.; SAVOLDO, B. Targeting cd138 in cancer. Publication number:WO2014138704 A1; Application number: PCT/US2014/022137; 2014.
2. Forman, S. J.; Wang, X. Cs1 targeted chimeric antigen receptor-modified t cells. Publication number: WO2016090369 A1; Application number PCT/US2015/064303; 2016.
3. Yu, J.; HOFMEISTER, C.; CHU, J. Cs1-specific chimeric antigen receptor engineered immune effector cells. Publication number: WO2014179759 A1; Application number: PCT/US2014/036684; 2014.
4. BROGDON, J.; Choi, E.; Ebersbach, H.; Glass, D.; Huet, H.; June, C. H.; Mannick, J.; MILONE, M. C.; Murphy, L.; PLESA, G. Treatment of cancer using humanized anti-bcma chimeric antigen receptor. Publication number: WO2016014565 A3; Application number: PCT/US2015/041378; 2016.
5. KOCHENDERFER, J. N. Chimeric antigen receptors targeting b-cell maturation antigen. Publication number: WO2013154760 A1; Application number PCT/US2013/032029; 2013.
6. Morgan, R.; FRIEDMAN, K. Bcma chimeric antigen receptors. Publication number: WO2016014789 A3; Application number: PCT/US2015/041722; 2016.
7. PULÉ, M.; YONG, K.; LEE, L.; DRAPER, B. Chimeric antigen receptor. Publication number: WO2015052538 A1; Application number: PCT/GB2014/053058; 2015.

The invention claimed is:

1. A method of treating a subject with multiple myeloma wherein at least a subpopulation of the cells of said multiple myeloma express B-cell maturation antigen, the method including:
    administering intravenously or intradermally a therapeutically effective amount of chimeric antigen receptor-expressing immune effector cells to the subject, wherein the chimeric antigen receptor comprises a B-cell maturation antigen-binding domain;
    wherein the chimeric antigen receptor-expressing immune effector cells were produced by transducing immune cells with an expression vector comprising a nucleotide sequence encoding said chimeric antigen receptor comprising the B-cell maturation antigen-binding domain, the nucleotide sequence operably linked to an expression control sequence, wherein the chimeric antigen receptor further comprises a transmembrane domain, an intracellular costimulatory signaling domain and an intracellular activation domain;
    wherein said immune cells are selected from the group consisting of human T lymphocytes, natural killer cells, NK-92 cells, and natural killer T cells,
    wherein the B-cell maturation antigen-binding domain comprises a variable heavy domain and a variable light domain,
    further wherein the variable heavy domain comprises a complementarity determining region 1 domain consisting of the amino acid sequence of SEQ ID NO:6, a complementarity determining region 2 domain consisting of the amino acid sequence of SEQ ID NO:8, and a complementarity determining region 3 domain consisting of the amino acid sequence of SEQ ID NO: 10, and wherein the variable light domain comprises includes complementarity determining region 1 domain consisting of the amino acid sequence of SEQ ID NO: 14, complementarity determining region 2 domain consisting of the amino acid sequence of SEQ ID NO:16, and complementarity determining region 3 domain consisting of the amino acid sequence of SEQ ID NO: 18 wherein the administration of the immune effector cells mediates the treatment of the multiple myeloma.

2. The method of claim 1, wherein the transmembrane domain of the chimeric antigen receptor is a functional signaling domain from a protein selected from the group consisting of the T cell receptor, CD28, CDS-ζ, CD45, CD8 and CD16.

3. The method of claim 1, wherein the transmembrane domain of the chimeric antigen receptor comprises the amino acid sequence of SEQ ID NO: 47.

4. The method of claim 1, wherein the intracellular costimulatory signaling domain of the chimeric antigen receptor is from a protein selected from the group consisting of OX40, CD27, CD28, ICAM-1, ICOS (CD278), and 4-1BB (CD137).

5. The method of claim 1, wherein the intracellular co-stimulatory domain of the chimeric antigen receptor comprises the amino acid sequence of SEQ ID NO: 49 and the amino acid sequence of SEQ ID NO: 53.

6. The method of claim 1, wherein the chimeric antigen receptor-expressing immune effector cells are administered in combination with a chemotherapeutic agent.

7. The method of claim 6, wherein the chemotherapeutic agent ameliorates side effects and/or increases therapeutic benefit of the chimeric antigen receptor-expressing immune effector cells in the subject.

8. The method of claim 1, wherein the variable heavy domain comprises the amino acid sequence of SEQ ID NO: 4 and the variable light domain comprises the amino acid sequence of SEQ ID NO: 12.

9. The method of claim 1, wherein the variable heavy domain comprises the amino acid sequence encoded by the nucleotide sequence of SEQ ID NO: 43 and the variable light domain comprises the amino acid sequence encoded by the nucleotide sequence of SEQ ID NO: 39.

* * * * *